United States Patent
Goodman et al.

(10) Patent No.: US 11,241,461 B2
(45) Date of Patent: *Feb. 8, 2022

(54) TREATING CANCER USING A BLAUTIA STRAIN

(71) Applicant: Evelo Biosciences, Inc., Cambridge, MA (US)

(72) Inventors: Brian Goodman, Jamaica Plain, MA (US); Peter Sandy, Revere, MA (US); Jacqueline Papkoff, San Francisco, CA (US); Humphrey Gardner, Marblehead, MA (US); Holly Ponichtera, Cambridge, MA (US)

(73) Assignee: Evelo Biosciences, Inc., Cambridge, MA (US)

(*) Notice: Subject to any disclaimer, the term of this patent is extended or adjusted under 35 U.S.C. 154(b) by 208 days.

This patent is subject to a terminal disclaimer.

(21) Appl. No.: 16/116,223

(22) Filed: Aug. 29, 2018

(65) Prior Publication Data
US 2019/0240267 A1 Aug. 8, 2019

Related U.S. Application Data

(60) Provisional application No. 62/696,429, filed on Jul. 11, 2018, provisional application No. 62/573,406, (Continued)

(51) Int. Cl.
*A61K 35/742* (2015.01)
*A61K 35/74* (2015.01)
(Continued)

(52) U.S. Cl.
CPC ............ *A61K 35/74* (2013.01); *A61K 35/742* (2013.01); *A61K 38/19* (2013.01); *A61K 38/193* (2013.01); *A61K 38/217* (2013.01); *A61K 39/395* (2013.01); *A61K 45/06* (2013.01); *A61P 35/00* (2018.01); *C12N 1/20* (2013.01); *C12N 1/205* (2021.05); *C12R 2001/01* (2021.05)

(58) Field of Classification Search
CPC .... A61K 35/74; A61K 38/193; A61K 35/742; A61K 45/06; C12R 1/01; C12R 2001/01; A61P 35/00; A61P 35/10; C12N 1/205
See application file for complete search history.

(56) References Cited

U.S. PATENT DOCUMENTS 10,493,113 B2 * 12/2019 Goodman .............. A61K 35/74

FOREIGN PATENT DOCUMENTS

| WO | WO-2014/121298 A2 | 8/2014 |
| WO | WO-2016/203218 A1 | 12/2016 |
| WO | WO-2019/046401 A1 | 3/2019 |

OTHER PUBLICATIONS

Ciernikova, et al., "Probiotic Survey in Cancer Patients Treated in the Outpatient Department in a Comprehensive Cancer Center," Integrative Cancer Therapies (2017), vol. 16(2): 188-195 (Year: 2017).*

(Continued)

*Primary Examiner* — David W Berke-Schlessel
*Assistant Examiner* — Trent R Clarke
(74) *Attorney, Agent, or Firm* — Foley Hoag LLP; Brendan T. Jones; Mohanad Mossalam

(57) ABSTRACT

Provided herein are methods and compositions related to *Blautia* Strain A useful as therapeutic agents.

15 Claims, 12 Drawing Sheets

Specification includes a Sequence Listing.

B16-F10

Related U.S. Application Data filed on Oct. 17, 2017, provisional application No. 62/551,554, filed on Aug. 29, 2017.

(51) Int. Cl.

| | |
|---|---|
| *A61P 35/00* | (2006.01) |
| *A61K 38/21* | (2006.01) |
| *A61K 38/19* | (2006.01) |
| *A61K 39/395* | (2006.01) |
| *C12N 1/20* | (2006.01) |
| *A61K 45/06* | (2006.01) |
| *C12R 1/01* | (2006.01) |

(56) References Cited

OTHER PUBLICATIONS

NPL document "Drugs Approved for Colon and Rectal Cancer" is a webpage from the National Cancer Institute, accessed at https://www.cancer.gov/about-cancer/treatment/drugs/colorectal on Mar. 18, 2021. (Year: 2021).*

NPL document "Drugs Approved for Leukemia" is a webpage from the National Cancer Institute, accessed at https://www.cancer.gov/about-cancer/treatment/drugs/leukemia on Mar. 18, 2021. (Year: 2021).*

NPL document "Alignment 1" is an alignment generated with the BLAST tool from NCBI at blast.ncbi.nlm.nih.gov performed on Mar. 30, 2021 using HM626177 as the query sequence and LN890282 as the subject sequence. (Year: 2021).*

NPL document "Alignment 2" is an alignment generated with the BLAST tool from NCBI at blast.ncbi.nlm.nih.gov performed on Mar. 30, 2021 using EF036467 as the query sequence and LN890282 as the subject sequence. (Year: 2021).*

Bard et al., "Relationship Between Intestinal Microbiota and Clinical Characteristics of Patients with Early Stage Breast Cancer," The FASEB Journal, 29(S1):914 (2015).

Chen et al., "Human intestinal lumen and mucosa-associated microbiota in patients with colorectal cancer," PloS one, 7(6):1-9 (2012).

Durand et al., "*Blautia massiliensis* sp. nov., isolated from a fresh human fecal sample and emended description of the genus Blautia," Anaerobe, 43(5):47-55 (2016).

International Search Report and Written Opinion for International Application No. PCT/US2018/048508 dated Jan. 8, 2019.

Liu et al., "Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb, nov., *Blautia hansenii* comb, nov., *Blautia hydrogenotrophica* comb, nov., *Blautia luti* comb, nov., *Blautia producta* comb, nov., *Blautia schinkii* comb. nov. and description of *Blautia wexlerae* sp. nov., isolated from human faeces," International journal of systematic and evolutionary microbiology, 58(8):1896-1902 (2008).

Luu et al., "Intestinal proportion of Blautia sp. is associated with clinical stage and histoprognostic grade in patients with early-stage breast cancer," Nutrition and cancer, 69(2):267-275 (2017).

Ming et al., "Strategies in fed-batch cultivation on the production performance of Lactobacillus salivarius I 24 viable cells," Food Science and Biotechnology, 25(5):1393-1398 (2016).

Shida et al., "Probiotics as efficient immunopotentiators: translational role in cancer prevention," The Indian journal of medical research, 138(5):808 (2013).

Zackular et al., "The gut microbiome modulates colon tumorigenesis," Mbio, 4(6):e00692-13 (2013).

Rosello-Mora et al., "The species concept for prokaryotes," FEMS Microbiology Reviews, 25: 39-67 (2001).

\* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagtttgat cmtggctcag                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tacggytacc ttgttacgac tt                                           22
```

TREATING CANCER USING A BLAUTIA STRAIN

RELATED APPLICATIONS

This application claims the benefit of priority to U.S. Provisional Patent Applications having Ser. Nos. 62/551,554, filed Aug. 29, 2017, 62/573,406, filed Oct. 17, 2017, and 62/696,429, filed Jul. 11, 2018, the contents of each of which are hereby incorporated herein by reference in their entirety.

SEQUENCE LISTING

The instant application contains a Sequence Listing which has been filed electronically in ASCII format and is hereby incorporated by reference in its entirety. Said ASCII copy, created on Nov. 19, 2018, is named ETB-008_01_SL.txt and is 799 bytes in size.

SUMMARY

In certain aspects, provided herein are methods and compositions related to the treatment of a cancer in a subject (e.g., a human subject) comprising administering a bacterial composition comprising *Blautia* Strain A. In some embodiments, the *Blautia* Strain A is *Blautia massiliensis* Strain A (ATCC Deposit Number PTA-125134). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence of the *Blautia* Strain A. In some embodiments, provided here are bioreactors comprising *Blautia* Strain A disclosed herein. In some embodiments, the administration of the bacterial composition induces an immune response against a tumor in the subject. In some embodiments, the administration of the bacterial composition treats the cancer in the subject. In some embodiments, the administration augments a tumor microenvironment in the subject. In some embodiments, the cancer is a colorectal carcinoma.

In certain embodiments, provided herein are methods of treating a subject who has cancer, comprising administering to the subject a bacterial composition comprising *Blautia* Strain A (e.g., a killed bacterium, a live bacterium and/or an attenuated bacterium). In some embodiments, the *Blautia* Strain A is *Blautia massiliensis* Strain A (ATCC Deposit Number PTA-125134). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence of the *Blautia* Strain A. In some embodiments, at least 50%, 60%, 70%, 80%, 85%, 90%, 90%, 91%, 92%, 93%, 94%, 95%, 96%, 97%, 98% or 99% of the bacteria in the bacterial composition are *Blautia* Strain A. In some embodiments, all or substantially all of the bacteria in the bacterial formulation are *Blautia* Strain A. In some embodiments, the bacterial formulation comprises at least $1\times10^5$, $5\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $1\times10^8$, $2\times10^8$, $3\times10^8$, $4\times10^8$, $5\times10^8$, $6\times10^8$, $7\times10^8$, $8\times10^8$, $9\times10^8$ or $1\times10^9$ colony forming units of *Blautia* Strain A.

In certain embodiments, provided herein are bacterial compositions comprising *Blautia* Strain A (e.g., a killed bacterium, a live bacterium and/or an attenuated bacterium). In some embodiments, at least 50%, 60%, 70%, 80%, 85%, 90%, 90%, 91%, 92%, 93%, 94%, 95%, 96%, 97%, 98% or 99% of the bacteria in the bacterial composition are *Blautia* Strain A. In some embodiments, the *Blautia* Strain A is *Blautia massiliensis* Strain A (ATCC Deposit Number PTA-125134). In some embodiments, the *Blautia* Strain A is a strain comprising at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence of the *Blautia* Strain A. In some embodiments, all or substantially all of the bacteria in the bacterial formulation are *Blautia* Strain A. In some embodiments, the bacterial formulation comprises at least $1\times10^5$, $5\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$ or $1\times10^9$ colony forming units of *Blautia* Strain A.

In some embodiments, the bacterial composition is administered orally, intravenously, intratumorally, or subcutaneously. In some embodiments, the bacterial composition is administered in 2 or more (e.g., 3 or more, 4 or more or 5 or more doses). In some embodiments, the administration to the subject of the two or more doses are separated by at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days or 21 days. In some embodiments, a second bacterium is administered as part of an ecological consortium.

In some embodiments, the method further comprises administering to the subject an antibiotic. In some embodiments, the method further comprises administering to the subject one or more other cancer therapies. In some embodiments, the other cancer therapy is the surgical removal of a tumor, the administration of a chemotherapeutic agent, the administration of radiation therapy, the administration of an antibiotic, the administration of a cancer immunotherapy (e.g., an immune checkpoint inhibitor, a cancer-specific antibody, a cancer vaccine, a primed antigen presenting cell, a cancer-specific T cell, a cancer-specific chimeric antigen receptor (CAR) T cell, an immune activating protein, an adjuvant), and/or the administration of another therapeutic bacterium.

In some embodiments, the subject is a mammal. In some embodiments, the subject is a human. In some embodiments, the subject is a non-human mammal (e.g., a dog, a cat, a cow, a horse, a pig, a donkey, a goat, a camel, a mouse, a rat, a guinea pig, a sheep, a llama, a monkey, a gorilla or a chimpanzee).

DETAILED DESCRIPTION

General

Figure 1:
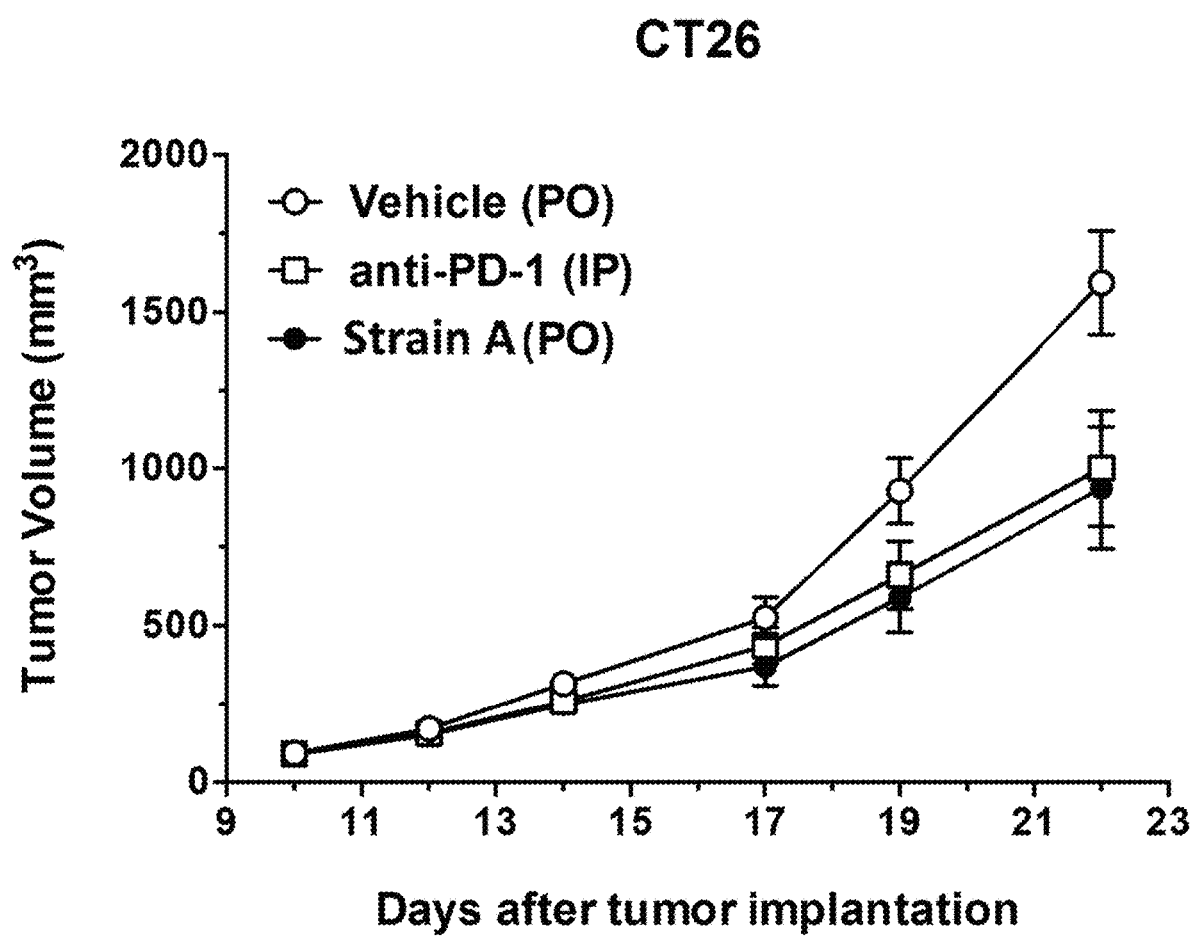
FIG. 1 shows that in a mouse colorectal carcinoma model, the efficacy of orally administered *Blautia* Strain A compared to that of intraperitoneally (i.p.) administered anti-PD-1.

In certain aspects, provided herein are methods of treating cancer in a subject comprising administering to the subject a bacterial composition comprising *Blautia* Strain A.

Definitions

"Adjuvant" or "Adjuvant therapy" broadly refers to an agent that affects an immunological or physiological response in a patient or subject. For example, an adjuvant might increase the presence of an antigen over time or to an area of interest like a tumor, help absorb an antigen presenting cell antigen, activate macrophages and lymphocytes and support the production of cytokines. By changing an immune response, an adjuvant might permit a smaller dose of an immune interacting agent to increase the effectiveness or safety of a particular dose of the immune interacting agent. For example, an adjuvant might prevent T cell exhaustion and thus increase the effectiveness or safety of a particular immune interacting agent.

"Administration" broadly refers to a route of administration of a composition to a subject. Examples of routes of administration include oral administration, rectal administration, topical administration, inhalation (nasal) or injection. Administration by injection includes intravenous (IV), intramuscular (IM), intratumoral (IT) and subcutaneous (SC) administration. The pharmaceutical compositions described herein can be administered in any form by any effective route, including but not limited to intratumoral, oral, parenteral, enteral, intravenous, intraperitoneal, topical, transdermal (e.g., using any standard patch), intradermal, ophthalmic, (intra)nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), intravesical, intrapulmonary, intraduodenal, intragastrical, and intrabronchial. In preferred embodiments, the pharmaceutical compositions described herein are administered orally, rectally, intratumorally, topically, intravesically, by injection into or adjacent to a draining lymph node, intravenously, by inhalation or aerosol, or subcutaneously.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')2, Fv, scFv, disulfide linked Fv, Fd, diabodies, single-chain antibodies, NANO-BODIES®, isolated CDRH3, and other antibody fragments that retain at least a portion of the variable region of an intact antibody. These antibody fragments can be obtained using conventional recombinant and/or enzymatic techniques and can be screened for antigen binding in the same manner as intact antibodies.

"Cancer" broadly refers to an uncontrolled, abnormal growth of a host's own cells leading to invasion of surrounding tissue and potentially tissue distal to the initial site of abnormal cell growth in the host. Major classes include carcinomas which are cancers of the epithelial tissue (e.g., skin, squamous cells); sarcomas which are cancers of the connective tissue (e.g., bone, cartilage, fat, muscle, blood vessels, etc.); leukemias which are cancers of blood forming tissue (e.g., bone marrow tissue); lymphomas and myelomas which are cancers of immune cells; and central nervous system cancers which include cancers from brain and spinal tissue. "Cancer(s)," "neoplasm(s)," and "tumor(s)" are used herein interchangeably. As used herein, "cancer" refers to all types of cancer or neoplasm or malignant tumors including leukemias, carcinomas and sarcomas, whether new or recurring. Specific examples of cancers are: carcinomas, sarcomas, myelomas, leukemias, lymphomas and mixed type tumors. Non-limiting examples of cancers are new or recurring cancers of the brain, melanoma, bladder, breast, cervix, colon, head and neck, kidney, lung, non-small cell lung, mesothelioma, ovary, prostate, sarcoma, stomach, uterus and medulloblastoma. Pediatric and adult tumors include, but not limited to, those of bladder, brain, breast, bone, cervix, colon, connective tissue, fat, head and neck, kidney, liver, lung, mesothelium, melanocytes (melanoma), muscle, ovary, pancreas, prostate, stomach, small intestine, and uterus The term "decrease" or "deplete" means a change, such that the difference is, depending on circumstances, at least 10%, 20%, 30%, 40%, 50%, 60%, 70%, 80%, 90%, 1/100, 1/1000, 1/10,000, 1/100,000, 1/1,000,000 or undetectable after treatment when compared to a pre-treatment state.

The term "ecological consortium" is a group of bacteria which trades metabolites and positively co-regulates one another, in contrast to two bacteria which induce host synergy through activating complementary host pathways for improved efficacy.

The term "epitope" means a protein determinant capable of specific binding to an antibody. Epitopes usually consist of chemically active surface groupings of molecules such as amino acids or sugar side chains. Certain epitopes can be defined by a particular sequence of amino acids to which an antibody is capable of binding.

The term "gene" is used broadly to refer to any nucleic acid associated with a biological function. The term "gene" applies to a specific genomic sequence, as well as to a cDNA or an mRNA encoded by that genomic sequence.

"Identity" as between nucleic acid sequences of two nucleic acid molecules can be determined as a percentage of identity using known computer algorithms such as the "FASTA" program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA Atschul, S. F., et al., J Molec Biol 215:403 (1990); Guide to Huge Computers, Mrtin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)).

"Immunotherapy" is treatment that uses a subject's immune system to treat cancer and includes, for example, checkpoint inhibitors, cancer vaccines, cytokines, cell therapy, CAR-T cells, and dendritic cell therapy.

The term "increase" means a change, such that the difference is, depending on circumstances, at least 10%, 20%, 30%, 40%, 50%, 60%, 70%, 80%, 90%, 2-fold, 4-fold, 10-fold, 100-fold, 10^3 fold, 10^4 fold, 10^5 fold, 10^6 fold, and/or 10^7 fold greater after treatment when compared to a pre-treatment state. Properties that may be increased include immune cells, bacterial cells, stromal cells, myeloid derived suppressor cells, fibroblasts, metabolites, and cytokines.

"Innate immune agonists" or "immuno-adjuvants" are small molecules, proteins, or other agents that specifically target innate immune receptors including Toll-Like Receptors, NOD receptors, STING Pathway components. For example, LPS is a TLR-4 agonist that is bacterially derived or synthesized and aluminum can be used as an immune stimulating adjuvant. immuno-adjuvants are a specific class of broader adjuvant or adjuvant therapy.

The term "isolated" or "enriched" encompasses a microbe, bacteria or other entity or substance that has been (1) separated from at least some of the components with which it was associated when initially produced (whether in nature or in an experimental setting), and/or (2) produced, prepared, purified, and/or manufactured by the hand of man. Isolated microbes may be separated from at least about 10%, about 20%, about 30%, about 40%, about 50%, about 60%, about 70%, about 80%, about 90%, or more of the other components with which they were initially associated. In some embodiments, isolated microbes are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a microbe or other material that has been separated from at least some of the components with which it was associated either when initially produced or generated (e.g., whether in nature or in an experimental setting), or during any time after its initial production. A microbe or a microbial population may be considered purified if it is isolated at or after production, such as from a material or environment containing the microbe or microbial population, and a purified microbe or microbial population may contain other materials up to about 10%, about 20%, about 30%, about 40%, about 50%, about 60%, about 70%, about 80%, about 90%, or above about 90% and still be considered "isolated." In some embodiments, purified microbes or microbial population are more than about 80%, about 85%, about 90%, about 91%, about 92%, about 93%, about 94%, about 95%, about 96%, about 97%, about 98%, about 99%, or more than about 99% pure. In the instance of microbial compositions provided herein, the one or more microbial types present in the composition can be independently purified from one or more other microbes produced and/or present in the material or environment containing the microbial type. Microbial compositions and the microbial components thereof are generally purified from residual habitat products.

As used herein, a gene is "overexpressed" in a bacteria if it is expressed at a higher level in an engineered bacteria under at least some conditions than it is expressed by a wild-type bacteria of the same species under the same conditions. Similarly, a gene is "underexpressed" in a bacteria if it is expressed at a lower level in an engineered bacteria under at least some conditions than it is expressed by a wild-type bacteria of the same species under the same conditions.

The terms "polynucleotide" and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

"Operational taxonomic units" and "OTU(s)" refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. For 16S, OTUs that share ≥97% average nucleotide identity across the entire 16S or some variable region of the 16S are considered the same OTU. See e.g. Claesson M J, Wang Q, O'Sullivan O, Greene-Diniz R, Cole J R, Ross R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940. For complete genomes, MLSTs, specific genes, other than 16S, or sets of genes OTUs that share ≥95% average nucleotide identity are considered the same OTU. See e.g., Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940. OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "housekeeping" genes), or a combination thereof. Operational Taxonomic Units (OTUs) with taxonomic assignments made to, e.g., genus, species, and phylogenetic clade are provided herein.

As used herein, "specific binding" refers to the ability of an antibody to bind to a predetermined antigen or the ability of a polypeptide to bind to its predetermined binding partner. Typically, an antibody or polypeptide specifically binds to its predetermined antigen or binding partner with an affinity corresponding to a $K_D$ of about $10^{-7}$ M or less, and binds to the predetermined antigen/binding partner with an affinity (as expressed by $K_D$) that is at least 10 fold less, at least 100 fold less or at least 1000 fold less than its affinity for binding to a non-specific and unrelated antigen/binding partner (e.g., BSA, casein). Alternatively, specific binding applies more broadly to a two component system where one component is a protein, lipid, or carbohydrate or combination thereof and engages with the second component which is a protein, lipid, carbohydrate or combination thereof in a specific way.

The terms "subject" or "patient" refers to any animal. A subject or a patient described as "in need thereof" refers to one in need of a treatment for a disease. Mammals (i.e., mammalian animals) include humans, laboratory animals (e.g., primates, rats, mice), livestock (e.g., cows, sheep, goats, pigs), and household pets (e.g., dogs, cats, rodents). For example, the subject may be a non-human mammal including but not limited to of a dog, a cat, a cow, a horse, a pig, a donkey, a goat, a camel, a mouse, a rat, a guinea pig, a sheep, a llama, a monkey, a gorilla or a chimpanzee. The subject or patient may be healthy, or may be suffering from a neoplasm at any developmental stage, wherein any of the stages are either caused by or opportunistically supported of a cancer associated or causative pathogen, or may be at risk of developing a neoplasm, or transmitting to others a cancer associated or cancer causative pathogen. In some embodiments patients have lung cancer, bladder cancer, prostate cancer, ovarian cancer, and/or melanoma. The patients may have tumors that show enhanced macropinocytosis with the underlying genomics of this process including Ras activation. In other embodiments patients suffer from other cancers. In some embodiments, the subject has undergone a cancer therapy.

"Strain" refers to a member of a bacterial species with a genetic signature such that it may be differentiated from closely-related members of the same bacterial species. The genetic signature may be the absence of all or part of at least one gene, the absence of all or part of at least on regulatory region (e.g., a promoter, a terminator, a riboswitch, a ribosome binding site), the absence ("curing") of at least one native plasmid, the presence of at least one recombinant gene, the presence of at least one mutated gene, the presence of at least one foreign gene (a gene derived from another species), the presence at least one mutated regulatory region (e.g., a promoter, a terminator, a riboswitch, a ribosome binding site), the presence of at least one non-native plasmid, the presence of at least one antibiotic resistance cassette, or a combination thereof. Genetic signatures between different strains may be identified by PCR amplification optionally followed by DNA sequencing of the genomic region(s) of interest or of the whole genome. In the case in which one strain (compared with another of the same species) has gained or lost antibiotic resistance or gained or lost a biosynthetic capability (such as an auxotrophic strain), strains may be differentiated by selection or counter-selection using an antibiotic or nutrient/metabolite, respectively.

As used herein, the term "treating" a disease in a subject or "treating" a subject having or suspected of having a disease refers to subjecting the subject to a pharmaceutical treatment, e.g., the administration of one or more agents, such that at least one symptom of the disease is decreased or prevented from worsening. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In certain embodiments, a cancer is treated if the subject experiences a reduction in tumor size, a reduced number of tumors, a reduction in tumor growth, a reduction in cancer metastasis and/or a reduced number of total cancer cells following treatment than would be expected in the absence of treatment.

Bacteria

In certain aspects, provided herein are methods of using a bacterial composition comprising *Blautia* Strain A. In some embodiments, the *Blautia* Strain A is *Blautia massiliensis* Strain A (ATCC Deposit Number PTA-125134). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence of the *Blautia* Strain A.

Under the terms of the Budapest Treaty on the International Recognition of the Deposit of Microorganisms for the Purpose of Patent Procedure, the *Blautia* Strain A was deposited on Jun. 7, 2018, with the American Type Culture Collection (ATCC) of 10801 University Boulevard, Manassas, Va. 20110-2209 USA and was assigned ATCC Accession Number PTA-125134.

Applicant represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant acknowledges its duty to replace the deposit should the depository be unable to furnish a sample when requested due to the condition of the deposit.

In some embodiments, the bacteria described herein are modified to improve colonization and/or engraftment in the mammalian gastrointestinal tract (e.g., modified metabolism, such as improved mucin degradation, enhanced competition profile, increased motility, increased adhesion to gut epithelial cells, modified chemotaxis). In some embodiments, the bacteria described herein are modified to enhance their immunomodulatory and/or therapeutic effect (e.g., either alone or in combination with another therapeutic agent). In some embodiments, the bacteria described herein are modified to enhance immune activation (e.g., through modified production of polysaccharides, pili, fimbriae, adhesins, outer membrane vesicles). In some embodiments, the bacteria described herein are modified to improve bacterial manufacturing (e.g., higher oxygen tolerance, improved freeze-thaw tolerance, shorter generation times).

*Blautia* Strain A can be cultured according to methods known in the art. For example, Blautia can be grown in ATCC Medium 2722, ATCC Medium 1490, or other medium using methods disclosed, for example in Caballero et al., 2017. "Cooperating Commensals Restore Colonization Resistance to Vancomycin-Resistant *Enterococcus faecium*" Cell Host & Microbe 21:592-602, which is hereby incorporated by reference in its entirety.

Bacterial Compositions

In certain aspects, provided herein are bacterial compositions comprising *Blautia* Strain A. In some embodiments, the *Blautia* Strain A is *Blautia massiliensis* Strain A (ATCC Deposit Number PTA-125134). In some embodiments, the *Blautia* Strain A is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence of the *Blautia* Strain A. In some embodiments, the bacterial formulation comprises a bacterium and/or a combination of bacteria described herein and a pharmaceutically acceptable carrier.

In certain embodiments, at least 50%, 55%, 60%, 65%, 70%, 75%, 80%, 85%, 90%, 91%, 92%, 93%, 94%, 95%, 96%, 97%, 98% or 99% of the bacteria in the bacterial composition are *Blautia* Strain A. In certain embodiments, substantially all of the bacteria in the bacterial composition are *Blautia* Strain A. In certain embodiments, the bacterial composition comprises at least $1\times10^3$ colony forming units (CFUs), $1\times10^4$ colony forming units (CFUs), $1\times10^5$ colony forming units (CFUs), $5\times10^5$ colony forming units (CFUs), $1\times10^6$ colony forming units (CFUs), $2\times10^6$ colony forming units (CFUs), $3\times10^6$ colony forming units (CFUs), $4\times10^6$ colony forming units (CFUs), $5\times10^6$ colony forming units (CFUs), $6\times10^6$ colony forming units (CFUs), $7\times10^6$ colony forming units (CFUs), $8\times10^6$ colony forming units (CFUs), $9\times10^6$ colony forming units (CFUs), $1\times10^7$ colony forming units (CFUs), $2\times10^7$ colony forming units (CFUs), $3\times10^7$ colony forming units (CFUs), $4\times10^7$ colony forming units (CFUs), $5\times10^7$ colony forming units (CFUs), $6\times10^7$ colony forming units (CFUs), $7\times10^7$ colony forming units (CFUs), $8\times10^7$ colony forming units (CFUs), $9\times10^7$ colony forming units (CFUs), $1\times10^8$ colony forming units (CFUs), $2\times10^8$ colony forming units (CFUs), $3\times10^8$ colony forming units (CFUs), $4\times10^8$ colony forming units (CFUs), $5\times10^8$ colony forming units (CFUs), $6\times10^8$ colony forming units (CFUs), $7\times10^8$ colony forming units (CFUs), $8\times10^8$ colony forming units (CFUs), $9\times10^8$ colony forming units (CFUs), $1\times10^9$ colony forming units (CFUs), $5\times10^9$ colony forming units (CFUs), $1\times10^{10}$ colony forming units (CFUs) $5\times10^{10}$ colony forming units (CFUs), $1\times10^{11}$ colony forming units (CFUs) $5\times10^{11}$ colony forming units (CFUs), $1\times10^{12}$ colony forming units (CFUs) $5\times10^{12}$ colony forming units (CFUs), $1\times10^{13}$ colony forming units (CFUs) of *Blautia* Strain A.

In some embodiments, at least 10%, 15%, 20%, 25%, 30%, 35%, 40%, 45%, 50%, 55%, 60%, 65%, 70%, 75%, 80%, 85%, 90%, 95%, 96%, 97%, 98% or 99% of the bacteria in the composition are selected from among the bacterial species described herein. 10%, 15%, 20%, 25%, 30%, 35%, 40%, 45%, 50%, 55%, 60%, 65%, 70%, 75%, 80%, 85%, 90%, 95%, 96%, 97%, 98% or 99% of the bacteria in the composition are selected from among the bacterial strains described herein.

In some embodiments, the compositions described herein may include only one species of bacteria described herein or may include two or more species of the bacteria described herein. For example, 1, 2, 3, 4, 5, 6, 7, 8, 9, 10, 11, 12, 13, 14, 15, 16, 17, 18, 19 or 20 of the species described herein, in any combination, can be included in the compositions provided herein.

As described in detail below, the pharmaceutical compositions disclosed herein may be specially formulated for administration in solid or liquid form, including those adapted for oral or rectal administration.

In some embodiments, the composition described herein may be a pharmaceutical composition, a dietary supplement, or a food product (e.g., a food or beverage). In some embodiments, the food product is an animal feed.

In certain embodiments, the pharmaceutical composition for oral administration described herein comprises an additional component that enables efficient delivery of the bacteria to the colon. In some embodiments, pharmaceutical preparation that enables the delivery of the bacteria to the colon can be used. Examples of such formulations include pH sensitive compositions, such as buffered sachet formulations or enteric polymers that release their contents when the pH becomes alkaline after the enteric polymers pass through the stomach. When a pH sensitive composition is used for formulating the pharmaceutical preparation, the pH sensitive composition can be a polymer whose pH threshold of the decomposition of the composition is between about 6.8 and about 7.5.

Another embodiment of a pharmaceutical composition useful for delivery of the bacteria to the colon is one that ensures the delivery to the colon by delaying the release of the bacteria by approximately 3 to 5 hours, which corresponds to the small intestinal transit time. In some embodiments, the pharmaceutical composition for delayed release includes a hydrogel shell. The hydrogel is hydrated and swells upon contact with gastrointestinal fluid, with the result that the contents are effectively released (released predominantly in the colon). Delayed release dosage units include bacteria-containing compositions having a material which coats or selectively coats the bacteria. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Examples of composition enabling the delivery to the colon further include bioadhesive compositions which specifically adhere to the colonic mucosal membrane (for example, a polymer described in the specification of U.S. Pat. No. 6,368,586, hereby incorporated by reference) and compositions into which a protease inhibitor is incorporated for protecting particularly a biopharmaceutical preparation in the gastrointestinal tracts from decomposition due to an activity of a protease.

An example of a system enabling the delivery to the colon is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

Another example of the system enabling the delivery to the colon is a system of delivering a composition to the colon, the system being specifically decomposed by an enzyme (for example, a carbohydrate hydrolase or a carbohydrate reductase) present in the colon. Such a system is not particularly limited, and more specific examples thereof include systems which use food components such as non-starch polysaccharides, amylose, xanthan gum, and azopolymers.

In some embodiments, formulations containing *Blautia* Strain A are provided as encapsulated, enteric coated, or powder forms, with doses ranging up to $10^{11}$ cfu (e.g., up to $10^{10}$ cfu). In some embodiments, the composition comprises $5 \times 10^{11}$ cfu of *Blautia* Strain A and 10% (w/w) corn starch in a capsule. The capsule is enteric coated for duodenal release at pH5.5 In some embodiments, the capsule is enteric coated for duodenal release at pH 5.5. In some embodiments, the composition comprises a powder of freeze-dried *Blautia* Strain A which is deemed "Qualified Presumption of Safety" (QPS) status. In some embodiments, the composition is stable at frozen or refrigerated temperature.

Methods for producing microbial compositions may include three main processing steps. The steps are: organism banking, organism production, and preservation. In certain embodiments, a sample that contains an abundance of *Blautia* Strain A may be cultured by avoiding an isolation step.

For banking, the strains included in the microbial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. Another example would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, *Handbook of Microbiological Media* (2010) CRC Press). Culture media can be added to the culture at the start, may be added during the culture, or may be intermittently/continuously flowed through the culture. The strains in the bacterial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For microbial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions, an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine-HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic conditions. If the microbial composition comprises, for example, spore forming species and results in the production of spores, the final composition may be purified by additional means such as density gradient centrifugation and preserved using the techniques [?]described above[?]. Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Microbial production may be conducted using similar culture steps to banking, including medium composition and culture conditions described above. It may be conducted at larger scales of operation, especially for clinical development or commercial production. At larger scales, there may be several subcultivations of the microbial composition prior to the final cultivation. At the end of cultivation, the culture is harvested to enable further formulation into a dosage form for administration. This can involve concentration, removal of undesirable medium components, and/or introduction into a chemical milieu that preserves the microbial composition and renders it acceptable for administration via the chosen route. For example, a microbial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

In certain aspects, provided are bacterial compositions for administration subjects. In some embodiments, the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments, the bacterial formulation comprises an enteric coating or micro encapsulation. In certain embodiments, the enteric coating or micro encapsulation improves targeting to a desired region of the gastrointestinal tract. For example, in certain embodiments, the bacterial composition comprises an enteric coating and/or microcapsules that dissolves at a pH associated with a particular region of the gastrointestinal tract. In some embodiments, the enteric coating and/or microcapsules dissolve at a pH of about 5.5-6.2 to release in the duodenum, at a pH value of about 7.2-7.5 to release in the ileum, and/or at a pH value of about 5.6-6.2 to release in the colon. Exemplary enteric coatings and microcapsules are described, for example, in U.S. Pat. Pub. No. 2016/0022592, which is hereby incorporated by reference in its entirety.

In some embodiments, the composition is a food product (e.g., a food or beverage) such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products, including biscuits, cookies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

In certain embodiments, the bacteria disclosed herein are administered in conjunction with a prebiotic to the subject. Prebiotics are carbohydrates which are generally indigestible by a host animal and are selectively fermented or metabolized by bacteria. Prebiotics may be short-chain carbohydrates (e.g., oligosaccharides) and/or simple sugars (e.g., mono- and di-saccharides) and/or mucins (heavily glycosylated proteins) that alter the composition or metabolism of a microbiome in the host. The short chain carbohydrates are also referred to as oligosaccharides, and usually contain from 2 or 3 and up to 8, 9, 10, 15 or more sugar moieties. When prebiotics are introduced to a host, the prebiotics affect the bacteria within the host and do not directly affect the host. In certain aspects, a prebiotic composition can selectively stimulate the growth and/or activity of one of a limited number of bacteria in a host. Prebiotics include oligosaccharides such as fructooligosaccharides (FOS) (including inulin), galactooligosaccharides (GOS), trans-galactooligosaccharides, xylooligosaccharides (XOS), chitooligosaccharides (COS), soy oligosaccharides (e.g., stachyose and raffinose) gentiooligosaccharides, isomaltooligosaccharides, mannooligosaccharides, maltooligosaccharides and mannanoligosaccharides. Oligosaccharides are not necessarily single components, and can be mixtures containing oligosaccharides with different degrees of oligomerization, sometimes including the parent disaccharide and the monomeric sugars. Various types of oligosaccharides are found as natural components in many common foods, including fruits, vegetables, milk, and honey. Specific examples of oligosaccharides are lactulose, lactosucrose, palatinose, glycosyl sucrose, guar gum, gum Arabic, tagalose, amylose, amylopectin, pectin, xylan, and cyclodextrins. Prebiotics may also be purified or chemically or enzymatically synthesized.

Administration

In certain aspects, provided herein is a method of delivering a bacterium and/or a bacterial composition described herein to a subject. In some embodiments of the methods provided herein, the bacteria are administered in conjunction with the administration of a cancer therapeutic. In some embodiments, the bacteria is co-formulated in a pharmaceutical composition with the cancer therapeutic. In some embodiments, the bacteria is co-administered with the cancer therapeutic. In some embodiments, the cancer therapeutic is administered to the subject before administration of the bacteria (e.g., about 1, 2, 3, 4, 5, 6, 7, 8, 9, 10, 15, 20, 25, 30, 35, 40, 45, 50 or 55 minutes before, about 1, 2, 3, 4, 5, 6, 7, 8, 9, 10, 11, 12, 13, 14, 15, 16, 17, 18, 19, 20, 21, 22 or 23 hours before, or about 1, 2, 3, 4, 5, 6, 7, 8, 9, 10, 11, 12, 13 or 14 days before). In some embodiments, the cancer therapeutic is administered to the subject after administration of the bacteria (e.g., about 1, 2, 3, 4, 5, 6, 7, 8, 9, 10, 15, 20, 25, 30, 35, 40, 45, 50 or 55 minutes after, about 1, 2, 3, 4, 5, 6, 7, 8, 9, 10, 11, 12, 13, 14, 15, 16, 17, 18, 19, 20, 21, 22 or 23 hours after, or about 1, 2, 3, 4, 5, 6, 7, 8, 9, 10, 11, 12, 13 or 14 days after). In some embodiments, the same mode of delivery is used to deliver both the bacteria and the cancer therapeutic. In some embodiments different modes of delivery are used to administer the bacteria and the cancer therapeutic. For example, in some embodiments, the bacteria is administered orally while the cancer therapeutic is administered via injection (e.g., an intravenous, intramuscular and/or intratumoral injection).

In certain embodiments, the pharmaceutical compositions, dosage forms, and kits described herein can be administered in conjunction with any other conventional anti-cancer treatment, such as, for example, radiation therapy and surgical resection of the tumor. These treatments may be applied as necessary and/or as indicated and may occur before, concurrent with or after administration of the pharmaceutical compositions, dosage forms, and kits described herein.

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular microorganism to be administered, duration and route of administration, the kind and stage of the disease, for example, tumor size, and other compounds such as drugs being administered concurrently. In addition to the above factors, such levels can be affected by the infectivity of the microorganism, and the nature of the microorganism, as can be determined by one skilled in the art. In the present methods, appropriate minimum dosage levels of microorganisms can be levels sufficient for the microorganism to survive, grow and replicate in a tumor or metastasis. The methods of treatment described herein may be suitable for the treatment of a primary tumor, a secondary tumor or metastasis, as well as for recurring tumors or cancers. The dose of the pharmaceutical compositions described herein may be appropriately set or adjusted in accordance with the dosage form, the route of administration, the degree or stage of a target disease, and the like. For example, the general effective dose of the agents may range between 0.01 mg/kg body weight/day and 1000 mg/kg body weight/day, between 0.1 mg/kg body weight/day and 1000 mg/kg body weight/day, 0.5 mg/kg body weight/day and 500 mg/kg body weight/day, 1 mg/kg body weight/day and 100 mg/kg body weight/day, or between 5 mg/kg body weight/day and 50 mg/kg body weight/day. The effective dose may be 0.01, 0.05, 0.1, 0.5, 1, 2, 3, 5, 10, 20, 30, 40, 50, 60, 70, 80, 90, 100, 200, 500, or 1000 mg/kg body weight/day or more, but the dose is not limited thereto.

In some embodiments, the dose administered to a subject is sufficient to prevent cancer, delay its onset, or slow or stop its progression or prevent a relapse of a cancer. One skilled in the art will recognize that dosage will depend upon a variety of factors including the strength of the particular compound employed, as well as the age, species, condition, and body weight of the subject. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. An effective dosage and treatment protocol can be determined by routine and conventional means, starting e.g., with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

In accordance with the above, in therapeutic applications, the dosages of the active agents used in accordance with the invention vary depending on the active agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and most preferably causing complete regression of the cancer.

Separate administrations can include any number of two or more administrations (e.g., doses), including two, three, four, five or six administrations. One skilled in the art can readily determine the number of administrations to perform, or the desirability of performing one or more additional administrations, according to methods known in the art for monitoring therapeutic methods and other monitoring methods provided herein. In some embodiments, the doses may be separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days or 1, 2, 3, or 4 weeks. Accordingly, the methods provided herein include methods of providing to the subject one or more administrations of a bacterium, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of tumor growth or inhibition of tumor growth, appearance of new metastases or inhibition of metastasis, the subject's anti-bacterium antibody titer, the subject's anti-tumor antibody titer, the overall health of the subject and/or the weight of the subject.

The time period between administrations can be any of a variety of time periods. The time period between administrations can be a function of any of a variety of factors, including monitoring steps, as described in relation to the number of administrations, the time period for a subject to mount an immune response and/or the time period for a subject to clear the bacteria from normal tissue. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the bacteria from normal tissue; for example, the time period can be more than the time period for a subject to clear the bacteria from normal tissue, such as more than about a day, more than about two days, more than about three days, more than about five days, or more than about a week.

In some embodiments, the delivery of a cancer therapeutic in combination with the bacteria described herein reduces the adverse effects and/or improves the efficacy of the cancer therapeutic.

The effective dose of a cancer therapeutic described herein is the amount of the therapeutic agent that is effective to achieve the desired therapeutic response for a particular patient, composition, and mode of administration, with the least toxicity to the patient. The effective dosage level can be identified using the methods described herein and will depend upon a variety of pharmacokinetic factors including the activity of the particular compositions administered, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. In general, an effective dose of a cancer therapy will be the amount of the therapeutic agent which is the lowest dose effective to produce a therapeutic effect. Such an effective dose will generally depend upon the factors described above.

The toxicity of a cancer therapy is the level of adverse effects experienced by the subject during and following treatment. Adverse events associated with cancer therapy toxicity include, but are not limited to, abdominal pain, acid indigestion, acid reflux, allergic reactions, alopecia, anaphylaxis, anemia, anxiety, lack of appetite, arthralgias, asthenia, ataxia, azotemia, loss of balance, bone pain, bleeding, blood clots, low blood pressure, elevated blood pressure, difficulty breathing, bronchitis, bruising, low white blood cell count, low red blood cell count, low platelet count, cardiotoxicity, cystitis, hemorrhagic cystitis, arrhythmias, heart valve disease, cardiomyopathy, coronary artery disease, cataracts, central neurotoxicity, cognitive impairment, confusion, conjunctivitis, constipation, coughing, cramping, cystitis, deep vein thrombosis, dehydration, depression, diarrhea, dizziness, dry mouth, dry skin, dyspepsia, dyspnea, edema, electrolyte imbalance, esophagitis, fatigue, loss of fertility, fever, flatulence, flushing, gastric reflux, gastroesophageal reflux disease, genital pain, granulocytopenia, gynecomastia, glaucoma, hair loss, hand-foot syndrome, headache, hearing loss, heart failure, heart palpitations, heartburn, hematoma, hemorrhagic cystitis, hepatotoxicity, hyperamylasemia, hypercalcemia, hyperchloremia, hyperglycemia, hyperkalemia, hyperlipasemia, hypermagnesemia, hypernatremia, hyperphosphatemia, hyperpigmentation, hypertriglyceridemia, hyperuricemia, hypoalbuminemia, hypocalcemia, hypochloremia, hypoglycemia, hypokalemia, hypomagnesemia, hyponatremia, hypophosphatemia, impotence, infection, injection site reactions, insomnia, iron deficiency, itching, joint pain, kidney failure, leukopenia, liver dysfunction, memory loss, menopause, mouth sores, mucositis, muscle pain, myalgias, myelosuppression, myocarditis, neutropenic fever, nausea, nephrotoxicity, neutropenia, nosebleeds, numbness, ototoxicity, pain, palmar-plantar erythrodysesthesia, pancytopenia, pericarditis, peripheral neuropathy, pharyngitis, photophobia, photosensitivity, pneumonia, pneumonitis, proteinuria, pulmonary embolus, pulmonary fibrosis, pulmonary toxicity, rash, rapid heart beat, rectal bleeding, restlessness, rhinitis, seizures, shortness of breath, sinusitis, thrombocytopenia, tinnitus, urinary tract infection, vaginal bleeding, vaginal dryness, vertigo, water retention, weakness, weight loss, weight gain, and xerostomia. In general, toxicity is acceptable if the benefits to the subject achieved through the therapy outweigh the adverse events experienced by the subject due to the therapy.

In some embodiments, the administration of the bacterial composition treats the cancer. In some embodiments, the bacterial composition induces an anti-tumor immune response in the subject.

Therapeutic Agents

In certain aspects, the methods provided herein include the administration to a subject of a bacterium and/or a bacterial composition described herein (e.g., a *Blautia* Strain A-containing bacterial composition) either alone or in combination with another cancer therapeutic. The other cancer therapeutic may include e.g., surgical resection, radiotherapy, or a cancer therapeutic agent. In some embodiments, the bacterial composition and the other cancer therapy can be administered to the subject in any order. In some embodiments, the bacterial composition and the other cancer therapy are administered conjointly.

In some embodiments the bacterium is administered to the subject before the cancer therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments the bacterium is administered to the subject after the cancer therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the bacterium and the cancer therapeutic are administered to the subject simultaneously or nearly simultaneously (e.g., administrations occur within an hour of each other). In some embodiments, the subject is administered an antibiotic before the bacterium is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments, the subject is administered an antibiotic after the bacterium is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the bacterium and the antibiotic are administered to the subject simultaneously or nearly simultaneously (e.g., administrations occur within an hour of each other).

In certain embodiments, the subject may undergo surgery. Types of surgery include but are not limited to preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). Upon excision of part of all of cancerous cells, tissue, or tumor, a cavity may be formed in the body.

In certain embodiments, the subject may undergo radiation therapy. Radiation therapy includes the administration or application of a radiotherapeutic agents and factors including but not limited to In addition to trays, UV-irradiation, microwaves, electronic emissions, and radioisotopes. The localized tumor site may be irradiated, including by one or more the above described forms of radiations. All of these factors may effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In certain aspects, the methods provided herein further comprise administering another cancer therapeutic to the subject.

In some embodiments, the cancer therapeutic is a chemotherapeutic agent. Examples of such chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In some embodiments, the cancer therapeutic is a cancer immunotherapy agent. Immunotherapy refers to a treatment that uses a subject's immune system to treat cancer, e.g., checkpoint inhibitors, cancer vaccines, cytokines, cell therapy, CAR-T cells, and dendritic cell therapy. Non-limiting examples of immunotherapies are checkpoint inhibitors include Nivolumab (BMS, anti-PD-1), Pembrolizumab (Merck, anti-PD-1), Ipilimumab (BMS, anti-CTLA-4), MEDI4736 (AstraZeneca, anti-PD-L1), and MPDL3280A (Roche, anti-PD-L1). Other immunotherapies may be tumor vaccines, such as Gardail, Cervarix, BCG, sipulencel-T, Gp100:209-217, AGS-003, DCVax-L, Algenpantucel-L, Tergenpantucel-L, TG4010, ProstAtak, Prostvac-V/R-TRICOM, Rindopepimul, E75 peptide acetate, IMA901, POL-103A, Belagenpumatucel-L, GSK1572932A, MDX-1279, GV1001, and Tecemotide. Immunotherapy may be administered via injection (e.g., intravenously, intratumorally, subcutaneously, or into lymph nodes), but may also be administered orally, topically, or via aerosol. Immunotherapies may comprise adjuvants such as cytokines.

In some embodiments, the immunotherapy agent is an immune checkpoint inhibitor. Immune checkpoint inhibition broadly refers to inhibiting the checkpoints that cancer cells can produce to prevent or downregulate an immune response. Examples of immune checkpoint proteins include, but are not limited to, CTLA4, PD-1, PD-L1, PD-L2, A2AR, B7-H3, B7-H4, BTLA, KIR, LAG3, TIM-3 or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, MEDI-4736, MSB-0020718C, AUR-012 and STI-A1010.

In certain embodiments, immune checkpoint inhibitors can be an inhibitory nucleic acid molecule (e.g., an siRNA molecule, an shRNA molecule or an antisense RNA molecule) that inhibits expression of an immune checkpoint protein that inhibits expression of an immune checkpoint protein.

In some embodiments, the immune checkpoint inhibitor is a siRNA molecule. Such siRNA molecules should include a region of sufficient homology to the target region, and be of sufficient length in terms of nucleotides, such that the siRNA molecule down-regulate target RNA (e.g., RNA of an immune checkpoint protein). The term "ribonucleotide" or "nucleotide" can, in the case of a modified RNA or nucleotide surrogate, also refer to a modified nucleotide, or surrogate replacement moiety at one or more positions. It is not necessary that there be perfect complementarity between the siRNA molecule and the target, but the correspondence must be sufficient to enable the siRNA molecule to direct sequence-specific silencing, such as by RNAi cleavage of the target RNA. In some embodiments, the sense strand need only be sufficiently complementary with the antisense strand to maintain the overall double-strand character of the molecule.

In addition, an siRNA molecule may be modified or include nucleoside surrogates. Single stranded regions of an siRNA molecule may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA molecule, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

Each strand of an siRNA molecule can be equal to or less than 35, 30, 25, 24, 23, 22, 21, or 20 nucleotides in length. In some embodiments, the strand is at least 19 nucleotides in length. For example, each strand can be between 21 and 25 nucleotides in length. In some embodiments, siRNA agents have a duplex region of 17, 18, 19, 29, 21, 22, 23, 24, or 25 nucleotide pairs, and one or more overhangs, such as one or two 3' overhangs, of 2-3 nucleotides.

In some embodiments, the immune checkpoint inhibitor is a shRNA molecule. A "small hairpin RNA" or "short hairpin RNA" or "shRNA" includes a short RNA sequence that makes a tight hairpin turn that can be used to silence gene expression via RNA interference. The shRNAs provided herein may be chemically synthesized or transcribed from a transcriptional cassette in a DNA plasmid. The shRNA hairpin structure is cleaved by the cellular machinery into siRNA, which is then bound to the RNA-induced silencing complex (RISC).

In some embodiments, shRNAs are about 15-60, 15-50, or 15-40 (duplex) nucleotides in length, about 15-30, 15-25, or 19-25 (duplex) nucleotides in length, or are about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, or about 20-24, 21-22, or 21-23 nucleotides in length, and the double-stranded shRNA is about 15-60, 15-50, 15-40, 15-30, 15-25, or 19-25 base pairs in length, or about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), or from about 19 to about 40 nucleotides in length (e.g., about 19-40, 19-35, 19-30, or 19-25 nucleotides in length), or from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In some embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional embodiments related to the shRNAs, as well as methods of designing and synthesizing such shRNAs, are described in U.S. patent application publication number 2011/0071208, the disclosure of which is herein incorporated by reference in its entirety for all purposes.

In some embodiments, the immune checkpoint inhibitor is an antisense oligonucleotide compounds that inhibits expression of an immune checkpoint protein. In certain embodiments, the degree of complementarity between the target sequence and antisense targeting sequence is sufficient to form a stable duplex. The region of complementarity of the antisense oligonucleotides with the target RNA sequence may be as short as 8-11 bases, but can be 12-15 bases or more, e.g., 10-40 bases, 12-30 bases, 12-25 bases, 15-25 bases, 12-20 bases, or 15-20 bases, including all integers in between these ranges. An antisense oligonucleotide of about 14-15 bases is generally long enough to have a unique complementary sequence.

In certain embodiments, antisense oligonucleotides may be 100% complementary to the target sequence, or may include mismatches, e.g., to improve selective targeting of allele containing the disease-associated mutation, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence. Oligonucleotide backbones that are less susceptible to cleavage by nucleases are discussed herein. Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability.

The inhibitory nucleic acid molecule can be prepared, for example, by chemical synthesis, in vitro transcription, or digestion of long dsRNA by Rnase III or Dicer. These can be introduced into cells by transfection, electroporation, or other methods known in the art. See Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052.

In the present methods, the inhibitory nucleic acid molecule can be administered to the subject, for example, as naked nucleic acid, in combination with a delivery reagent, and/or as a nucleic acid comprising sequences that express an interfering nucleic acid molecule. In some embodiments the nucleic acid comprising sequences that express the interfering nucleic acid molecules are delivered within vectors, e.g. plasmid, viral and bacterial vectors. Any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Res., 32(13):e109 (2004); Hanai et al. Ann NY Acad Sci., 1082:9-17 (2006); and Kawata et al. Mol Cancer Ther., 7(9):2904-12 (2008); each of which is incorporated herein in their entirety. Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference in its entirety.

In some embodiments, the immunotherapy agent is an antibody or antigen binding fragment thereof that, for example, binds to a cancer-associated antigen. Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3,4,5,6,7, GAS7, glypican-3, GnTV, gp100/Pmel17, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, ME1, Melan-A/MART-1, Meloe, Midkine, MMP-2, MMP-7, MUC1, MUC5AC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAX5, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGS5, RhoC, RNF43, RU2AS, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen.

In some embodiments, the immunotherapy agent is a cancer vaccine and/or a component of a cancer vaccine (e.g., an antigenic peptide and/or protein). The cancer vaccine can be a protein vaccine, a nucleic acid vaccine or a combination thereof. For example, in some embodiments, the cancer vaccine comprises a polypeptide comprising an epitope of a cancer-associated antigen. In some embodiments, the cancer vaccine comprises a nucleic acid (e.g., DNA or RNA, such as mRNA) that encodes an epitope of a cancer-associated antigen. In some embodiments, the nucleic acid is a vector (e.g., a bacterial vector, viral vector). Examples of bacterial vectors include, but are not limited to, *Mycobacterium bovis* (BCG), *Salmonella Typhimurium* ssp., *Salmonella Typhi* ssp., *Clostridium* sp. spores, *Escherichia coli* Nissle 1917, *Escherichia coli* K-12/LLO, *Listeria monocytogenes*, and *Shigella flexneri*. Examples of viral vectors include, but are not limited to, vaccinia, adenovirus, RNA viruses, and replication-defective avipox, replication-defective fowlpox, replication-defective canarypox, replication-defective MVA and replication-defective adenovirus.

In some embodiments, the cancer immunotherapy comprises administration of an antigen presenting cell (APC) primed with a cancer-specific antigen. In some embodiments, the APC is a dendritic cell, a macrophage or a B cell.

Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3,4,5,6,7, GAS7, glypican-3, GnTV, gp100/Pmel 17, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, ME1, Melan-A/MART-1, Meloe, Midkine, MMP-2, MMP-7, MUC1, MUC5AC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAX5, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGS5, RhoC, RNF43, RU2AS, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen.

In some embodiments, the cancer immunotherapy comprises administration of a cancer-specific chimeric antigen receptor (CAR). In some embodiments, the CAR is administered on the surface of a T cell. In some embodiments, the CAR binds specifically to a cancer-associated antigen.

In some embodiments, the cancer immunotherapy comprises administration of a cancer-specific T cell to the subject. In some embodiments, the T cell is a CD4$^+$ T cell. In some embodiments, the CD4$^+$ T cell is a $T_H1$ T cell, a $T_H2$ T cell or a $T_H17$ T cell. In some embodiments, the T cell expresses a T cell receptor specific for a cancer-associated antigen.

In some embodiments, the cancer vaccine is administered with an adjuvant. Examples of adjuvants include, but are not limited to, an immune modulatory protein, Adjuvant 65, α-GalCer, aluminum phosphate, aluminum hydroxide, calcium phosphate, β-Glucan Peptide, CpG DNA, GPI-0100, lipid A, lipopolysaccharide, Lipovant, Montanide, N-acetyl-muramyl-L-alanyl-D-isoglutamine, Pam3CSK4, quil A and trehalose dimycolate.

In some embodiments, the immunotherapy agent is an immune modulating protein to the subject. In some embodiments, the immune modulatory protein is a cytokine. Examples of immune modulating proteins include, but are not limited to, B lymphocyte chemoattractant ("BLC"), C-C motif chemokine 11 ("Eotaxin-1"), Eosinophil chemotactic protein 2 ("Eotaxin-2"), Granulocyte colony-stimulating factor ("G-CSF"), Granulocyte macrophage colony-stimulating factor ("GM-CSF"), 1-309, Intercellular Adhesion Molecule 1 ("ICAM-1"), Interferon gamma ("IFN-gamma"), Interlukin-1 alpha ("IL-1 alpha"), Interlukin-1 beta ("IL-1 beta"), Interleukin 1 receptor antagonist ("IL-1 ra"), Interleukin-2 ("IL-2"), Interleukin-4 ("IL-4"), Interleukin-5 ("IL-5"), Interleukin-6 ("IL-6"), Interleukin-6 soluble receptor ("IL-6 sR"), Interleukin-7 ("IL-7"), Interleukin-8 ("IL-8"), Interleukin-10 ("IL-10"), Interleukin-11 ("IL-11"), Subunit beta of Interleukin-12 ("IL-12 p40" or "IL-12 p70"), Interleukin-13 ("IL-13"), Interleukin-15 ("IL-15"), Interleukin-16 ("IL-16"), Interleukin-17 ("IL-17"), Chemokine (C-C motif) Ligand 2 ("MCP-1"), Macrophage colony-stimulating factor ("M-CSF"), Monokine induced by gamma interferon ("MIG"), Chemokine (C-C motif) ligand 2 ("MIP-1 alpha"), Chemokine (C-C motif) ligand 4 ("MIP-1 beta"), Macrophage inflammatory protein-1-delta ("MIP-1 delta"), Platelet-derived growth factor subunit B ("PDGF-BB"), Chemokine (C-C motif) ligand 5, Regulated on Activation, Normal T cell Expressed and Secreted ("RANTES"), TIMP metallopeptidase inhibitor 1 ("TIMP-1"), TIMP metallopeptidase inhibitor 2 ("TIMP-2"), Tumor necrosis factor, lymphotoxin-alpha ("TNF alpha"), Tumor necrosis factor, lymphotoxin-beta ("TNF beta"), Soluble TNF receptor type 1 ("sTNFRI"), sTNFRIIAR, Brain-derived neurotrophic factor ("BDNF"), Basic fibroblast growth factor ("bFGF"), Bone morphogenetic protein 4 ('BMP-4'), Bone morphogenetic protein 5 ("BMP-5"), Bone morphogenetic protein 7 ("BMP-7"), Nerve growth factor ("b-NGF"), Epidermal growth factor ("EGF"), Epidermal growth factor receptor ("EGFR"), Endocrine-gland-derived vascular endothelial growth factor ("EG-VEGF"), Fibroblast growth factor 4 ("FGF-4"), Keratinocyte growth factor ("FGF-7"), Growth differentiation factor 15 ("GDF-15"), Glial cell-derived neurotrophic factor ("GDNF"), Growth Hormone, Heparin-binding EGF-like growth factor ("HB-EGF"), Hepatocyte growth factor ("HGF"), Insulin-like growth factor binding protein 1 ("IGFBP-1"), Insulin-like growth factor binding protein 2 ("IGFBP-2"), Insulin-like growth factor binding protein 3 ("IGFBP-3"), Insulin-like growth factor binding protein 4 ("IGFBP-4"), Insulin-like growth factor binding protein 6 ("IGFBP-6"), Insulin-like growth factor 1 ("IGF-1"), Insulin, Macrophage colony-stimulating factor ("M-CSF R"), Nerve growth factor receptor ("NGF R"), Neurotrophin-3 ("NT-3"), Neurotrophin-4 ("NT-4"), Osteoclastogenesis inhibitory factor ("Osteoprotegerin"), Platelet-derived growth factor receptors ("PDGF-AA"), Phosphatidylinositol-glycan biosynthesis ("PIGF"), Skp, Cullin, F-box containing complex ("SCF"), Stem cell factor receptor ("SCF R"), Transforming growth factor alpha ("TGFalpha"), Transforming growth factor beta-1 ("TGF beta 1"), Transforming growth factor beta-3 ("TGF beta 3"), Vascular endothelial growth factor ("VEGF"), Vascular endothelial growth factor receptor 2 ("VEGFR2"), Vascular endothelial growth factor receptor 3 ("VEGFR3"), VEGF-D 6Ckine, Tyrosine-protein kinase receptor UFO ("Axl"), Betacellulin ("BTC"), Mucosae-associated epithelial chemokine ("CCL28"), Chemokine (C-C motif) ligand 27 ("CTACK"), Chemokine (C-X-C motif) ligand 16 ("CXCL16"), C-X-C motif chemokine 5 ("ENA-78"), Chemokine (C-C motif) ligand 26 ("Eotaxin-3"), Granulocyte chemotactic protein 2 ("GCP-2"), GRO, Chemokine (C-C motif) ligand 14 ("HCC-1"), Chemokine (C-C motif) ligand 16 ("HCC-4"), Interleukin-9 ("IL-9"), Interleukin-17 F ("IL-17F"), Interleukin-18-binding protein ("IL-18 BPa"), Interleukin-28 A ("IL-28A"), Interleukin 29 ("IL-29"), Interleukin 31 ("IL-31"), C-X-C motif chemokine 10 ("IP-10"), Chemokine receptor CXCR3 ("I-TAC"), Leukemia inhibitory factor ("LIF"), Light, Chemokine (C motif) ligand ("Lymphotactin"), Monocyte chemoattractant protein 2 ("MCP-2"), Monocyte chemoattractant protein 3 ("MCP-3"), Monocyte chemoattractant protein 4 ("MCP-4"), Macrophage-derived chemokine ("MDC"), Macrophage migration inhibitory factor ("MIF"), Chemokine (C-C motif) ligand 20 ("MIP-3 alpha"), C-C motif chemokine 19 ("MIP-3 beta"), Chemokine (C-C motif) ligand 23 ("MPIF-1"), Macrophage stimulating protein alpha chain ("MSPalpha"), Nucleosome assembly protein 1-like 4 ("NAP-2"), Secreted phosphoprotein 1 ("Osteopontin"), Pulmonary and activation-regulated cytokine ("PARC"), Platelet factor 4 ("PF4"), Stroma cell-derived factor-1 alpha ("SDF-1 alpha"), Chemokine (C-C motif) ligand 17 ("TARC"), Thymus-expressed chemokine ("TECK"), Thymic stromal lymphopoietin ("TSLP 4-IBB"), CD 166 antigen ("ALCAM"), Cluster of Differentiation 80 ("B7-1"), Tumor necrosis factor receptor superfamily member 17 ("BCMA"), Cluster of Differentiation 14 ("CD14"), Cluster of Differentiation 30 ("CD30"), Cluster of Differentiation 40 ("CD40 Ligand"), Carcinoembryonic antigen-related cell adhesion molecule 1 (biliary glycoprotein) ("CEACAM-1"), Death Receptor 6 ("DR6"), Deoxythymidine kinase ("Dtk"), Type 1 membrane glycoprotein ("Endoglin"), Receptor tyrosine-protein kinase erbB-3 ("ErbB3"), Endothelial-leukocyte adhesion molecule 1 ("E-Selectin"), Apoptosis antigen 1 ("Fas"), Fms-like tyrosine kinase 3 ("Flt-3L"), Tumor necrosis factor receptor superfamily member 1 ("GITR"), Tumor necrosis factor receptor superfamily member 14 ("HVEM"), Intercellular adhesion molecule 3 ("ICAM-3"), IL-1 R4, IL-1 RI, IL-10 Rbeta, IL-17R, IL-2Rgamma, IL-21R, Lysosome membrane protein 2 ("LIMPII"), Neutrophil gelatinase-associated lipocalin ("Lipocalin-2"), CD62L ("L-Selectin"), Lymphatic endothelium ("LYVE-1"), MHC class I polypeptide-related sequence A ("MICA"), MHC class I polypeptide-related sequence B ("MICB"), NRG1-beta1, Beta-type platelet-derived growth factor receptor ("PDGF Rbeta"), Platelet endothelial cell adhesion molecule ("PECAM-1"), RAGE, Hepatitis A virus cellular receptor 1 ("TIM-1"), Tumor necrosis factor receptor superfamily member IOC ("TRAIL R3"), Trappin protein transglutaminase binding domain ("Trappin-2"), Urokinase receptor ("uPAR"), Vascular cell adhesion protein 1 ("VCAM-1"), XEDARActivin A, Agouti-related protein ("AgRP"), Ribonuclease 5 ("Angiogenin"), Angiopoietin 1, Angiostatin, Catheprin S, CD40, Cryptic family protein D3 ("Cripto-1"), DAN, Dickkopf-related protein 1 ("DKK-1"), E-Cadherin, Epithelial cell adhesion molecule ("EpCAM"), Fas Ligand (FasL or CD95L), Fcg RIIB/C, FoUistatin, Galectin-7, Intercellular adhesion molecule 2 ("ICAM-2"), IL-13 R1, IL-13R2, IL-17B, IL-2 Ra, IL-2 Rb, IL-23, LAP, Neuronal cell adhesion molecule ("NrCAM"), Plasminogen activator inhibitor-1 ("PAI-1"), Platelet derived growth factor receptors ("PDGF-AB"), Resistin, stromal cell-derived factor 1 ("SDF-1 beta"), sgp130, Secreted frizzled-related protein 2 ("ShhN"), Sialic acid-binding immunoglobulin-type lectins ("Siglec-5"), ST2, Transforming growth factor-beta 2 ("TGF beta 2"), Tie-2, Thrombopoietin ("TPO"), Tumor necrosis factor receptor superfamily member 10D ("TRAIL R4"), Triggering receptor expressed on myeloid cells 1 ("TREM-1"), Vascular endothelial growth factor C ("VEGF-C"), VEGFR1Adiponectin, Adipsin ("AND"), Alpha-fetoprotein ("AFP"), Angiopoietin-like 4 ("ANGPTL4"), Beta-2-microglobulin ("B2M"), Basal cell adhesion molecule ("BCAM"), Carbohydrate antigen 125 ("CA125"), Cancer Antigen 15-3 ("CA15-3"), Carcinoembryonic antigen ("CEA"), cAMP receptor protein ("CRP"), Human Epidermal Growth Factor Receptor 2 ("ErbB2"), Follistatin, Follicle-stimulating hormone ("FSH"), Chemokine (C-X-C motif) ligand 1 ("GRO alpha"), human chorionic gonadotropin ("beta HCG"), Insulin-like growth factor 1 receptor ("IGF-1 sR"), IL-1 sRII, IL-3, IL-18 Rb, IL-21, Leptin, Matrix metalloproteinase-1 ("MMP-1"), Matrix metalloproteinase-2 ("MMP-2"), Matrix metalloproteinase-3 ("MMP-3"), Matrix metalloproteinase-8 ("MMP-8"), Matrix metalloproteinase-9 ("MMP-9"), Matrix metalloproteinase-10 ("MMP-10"), Matrix metalloproteinase-13 ("MMP-13"), Neural Cell Adhesion Molecule ("NCAM-1"), Entactin ("Nidogen-1"), Neuron specific enolase ("NSE"), Oncostatin M ("OSM"), Procalcitonin, Prolactin, Prostate specific antigen ("PSA"), Sialic acid-binding Ig-like lectin 9 ("Siglec-9"), ADAM 17 endopeptidase ("TACE"), Thyroglobulin, Metalloproteinase inhibitor 4 ("TIMP-4"), TSH2B4, Disintegrin and metalloproteinase domain-containing protein 9 ("ADAM-9"), Angiopoietin 2, Tumor necrosis factor ligand superfamily member 13/Acidic leucine-rich nuclear phosphoprotein 32 family member B ("APRIL"), Bone morphogenetic protein 2 ("BMP-2"), Bone morphogenetic protein 9 ("BMP-9"), Complement component 5a ("C5a"), Cathepsin L, CD200, CD97, Chemerin, Tumor necrosis factor receptor superfamily member 6B ("DcR3"), Fatty acid-binding protein 2 ("FABP2"), Fibroblast activation protein, alpha ("FAP"), Fibroblast growth factor 19 ("FGF-19"), Galectin-3, Hepatocyte growth factor receptor ("HGF R"), IFN-gammalpha/beta R2, Insulin-like growth factor 2 ("IGF-2"), Insulin-like growth factor 2 receptor ("IGF-2 R"), Interleukin-1 receptor 6 ("IL-1R6"), Interleukin 24 ("IL-24"), Interleukin 33 ("IL-33", Kallikrein 14, Asparaginyl endopeptidase ("Legumain"), Oxidized low-density lipoprotein receptor 1 ("LOX-1"), Mannose-binding lectin ("MBL"), Neprilysin ("NEP"), Notch homolog 1, translocation-associated (*Drosophila*) ("Notch-1"), Nephroblastoma overexpressed ("NOV"), Osteoactivin, Programmed cell death protein 1 ("PD-1"), N-acetylmuramoyl-L-alanine amidase ("PGRP-5"), Serpin A4, Secreted frizzled related protein 3 ("sFRP-3"), Thrombomodulin, Tolllike receptor 2 ("TLR2"), Tumor necrosis factor receptor superfamily member 10A ("TRAIL R1"), Transferrin ("TRF"), WIF-1ACE-2, Albumin, AMICA, Angiopoietin 4, B-cell activating factor ("BAFF"), Carbohydrate antigen 19-9 ("CA19-9"), CD 163, Clusterin, CRT AM, Chemokine (C-X-C motif) ligand 14 ("CXCL14"), Cystatin C, Decorin ("DCN"), Dickkopf-related protein 3 ("Dkk-3"), Delta-like protein 1 ("DLL1"), Fetuin A, Heparin-binding growth factor 1 ("aFGF"), Folate receptor alpha ("FOLR1"), Furin, GPCR-associated sorting protein 1 ("GASP-1"), GPCR-associated sorting protein 2 ("GASP-2"), Granulocyte colony-stimulating factor receptor ("GCSF R"), Serine protease hepsin ("HAI-2"), Interleukin-17B Receptor ("IL-17B R"), Interleukin 27 ("IL-27"), Lymphocyte-activation gene 3 ("LAG-3"), Apolipoprotein A-V ("LDL R"), Pepsinogen I, Retinol binding protein 4 ("RBP4"), SOST, Heparan sulfate proteoglycan ("Syndecan-1"), Tumor necrosis factor receptor superfamily member 13B ("TACI"), Tissue factor pathway inhibitor ("TFPI"), TSP-1, Tumor necrosis factor receptor superfamily, member 10b ("TRAIL R2"), TRANCE, Troponin I, Urokinase Plasminogen Activator ("uPA"), Cadherin 5, type 2 or VE-cadherin (vascular endothelial) also known as CD144 ("VE-Cadherin"), WNT1-inducible-signaling pathway protein 1 ("WISP-1"), and Receptor Activator of Nuclear Factor κ B ("RANK").

In some embodiments, the cancer therapeutic is a radioactive moiety that comprises a radionuclide. Exemplary radionuclides include, but are not limited to Cr-51, Cs-131, Ce-134, Se-75, Ru-97, I-125, Eu-149, Os-189m, Sb-119, I-123, Ho-161, Sb-117, Ce-139, In-111, Rh-103m, Ga-67, T1-201, Pd-103, Au-195, Hg-197, Sr-87m, Pt-191, P-33, Er-169, Ru-103, Yb-169, Au-199, Sn-121, Tm-167, Yb-175, In-113m, Sn-113, Lu-177, Rh-105, Sn-117m, Cu-67, Sc-47, Pt-195m, Ce-141, I-131, Tb-161, As-77, Pt-197, Sm-153, Gd-159, Tm-173, Pr-143, Au-198, Tm-170, Re-186, Ag-111, Pd-109, Ga-73, Dy-165, Pm-149, Sn-123, Sr-89, Ho-166, P-32, Re-188, Pr-142, Ir-194, In-114m/In-114, and Y-90.

In some embodiments, the cancer therapeutic is an angiogenesis inhibitor to the subject. Examples of such angiogenesis inhibitors include, but are not limited to Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometrig™).

In some embodiments, the cancer therapeutic is an antibiotic. For example, if the presence of a cancer-associated bacteria and/or a cancer-associated microbiome profile is detected according to the methods provided herein, antibiotics can be administered to eliminate the cancer-associated bacteria from the subject. "Antibiotics" broadly refers to compounds capable of inhibiting or preventing a bacterial infection. Antibiotics can be classified in a number of ways, including their use for specific infections, their mechanism of action, their bioavailability, or their spectrum of target microbe (e.g., Gram-negative vs. Gram-positive bacteria, aerobic vs. anaerobic bacteria, etc.) and these may be used to kill specific bacteria in specific areas of the host ("niches") (Leekha, et al 2011. General Principles of Antimicrobial Therapy. Mayo Clin Proc. 86(2): 156-167). In certain embodiments, antibiotics can be used to selectively target bacteria of a specific niche. In some embodiments, antibiotics known to treat a particular infection that includes a cancer niche may be used to target cancer-associated microbes, including cancer-associated bacteria in that niche. In other embodiments, antibiotics are administered after the bacterial treatment. In some embodiments, antibiotics are administered after the bacterial treatment to remove the engraftment.

In some aspects, antibiotics can be selected based on their bactericidal or bacteriostatic properties. Bactericidal antibiotics include mechanisms of action that disrupt the cell wall (e.g., β-lactams), the cell membrane (e.g., daptomycin), or bacterial DNA (e.g., fluoroquinolones). Bacteriostatic agents inhibit bacterial replication and include sulfonamides, tetracyclines, and macrolides, and act by inhibiting protein synthesis. Furthermore, while some drugs can be bactericidal in certain organisms and bacteriostatic in others, knowing the target organism allows one skilled in the art to select an antibiotic with the appropriate properties. In certain treatment conditions, bacteriostatic antibiotics inhibit the activity of bactericidal antibiotics. Thus, in certain embodiments, bactericidal and bacteriostatic antibiotics are not combined.

Antibiotics include, but are not limited to aminoglycosides, ansamycins, carbacephems, carbapenems, cephalosporins, glycopeptides, lincosamides, lipopeptides, macrolides, monobactams, nitrofurans, oxazolidonones, penicillins, polypeptide antibiotics, quinolones, fluoroquinolone, sulfonamides, tetracyclines, and anti-mycobacterial compounds, and combinations thereof.

Aminoglycosides include, but are not limited to Amikacin, Gentamicin, Kanamycin, Neomycin, Netilmicin, Tobramycin, Paromomycin, and Spectinomycin. Aminoglycosides are effective, e.g., against Gram-negative bacteria, such as *Escherichia coli, Klebsiella, Pseudomonas aeruginosa*, and *Francisella tularensis*, and against certain aerobic bacteria but less effective against obligate/facultative anaerobes. Aminoglycosides are believed to bind to the bacterial 30S or 50S ribosomal subunit thereby inhibiting bacterial protein synthesis.

Ansamycins include, but are not limited to, Geldanamycin, Herbimycin, Rifamycin, and Streptovaricin. Geldanamycin and Herbimycin are believed to inhibit or alter the function of Heat Shock Protein 90.

Carbacephems include, but are not limited to, Loracarbef. Carbacephems are believed to inhibit bacterial cell wall synthesis.

Carbapenems include, but are not limited to, Ertapenem, Doripenem, Imipenem/Cilastatin, and Meropenem. Carbapenems are bactericidal for both Gram-positive and Gram-negative bacteria as broad-spectrum antibiotics. Carbapenems are believed to inhibit bacterial cell wall synthesis.

Cephalosporins include, but are not limited to, Cefadroxil, Cefazolin, Cefalotin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, and Ceftobiprole. Selected Cephalosporins are effective, e.g., against Gram-negative bacteria and against Gram-positive bacteria, including *Pseudomonas*, certain Cephalosporins are effective against methicillin-resistant *Staphylococcus aureus* (MRSA). Cephalosporins are believed to inhibit bacterial cell wall synthesis by disrupting synthesis of the peptidoglycan layer of bacterial cell walls.

Glycopeptides include, but are not limited to, Teicoplanin, Vancomycin, and Telavancin. Glycopeptides are effective, e.g., against aerobic and anaerobic Gram-positive bacteria including MRSA and *Clostridium difficile*. Glycopeptides are believed to inhibit bacterial cell wall synthesis by disrupting synthesis of the peptidoglycan layer of bacterial cell walls.

Lincosamides include, but are not limited to, Clindamycin and Lincomycin. Lincosamides are effective, e.g., against anaerobic bacteria, as well as *Staphylococcus*, and *Streptococcus*. Lincosamides are believed to bind to the bacterial 50S ribosomal subunit thereby inhibiting bacterial protein synthesis.

Lipopeptides include, but are not limited to, Daptomycin. Lipopeptides are effective, e.g., against Gram-positive bacteria. Lipopeptides are believed to bind to the bacterial membrane and cause rapid depolarization.

Macrolides include, but are not limited to, Azithromycin, Clarithromycin, Dirithromycin, Erythromycin, Roxithromycin, Troleandomycin, Telithromycin, and Spiramycin. Macrolides are effective, e.g., against *Streptococcus* and *Mycoplasma*. Macrolides are believed to bind to the bacterial or 50S ribosomal subunit, thereby inhibiting bacterial protein synthesis.

Monobactams include, but are not limited to, Aztreonam. Monobactams are effective, e.g., against Gram-negative bacteria. Monobactams are believed to inhibit bacterial cell wall synthesis by disrupting synthesis of the peptidoglycan layer of bacterial cell walls.

Nitrofurans include, but are not limited to, Furazolidone and Nitrofurantoin.

Oxazolidonones include, but are not limited to, Linezolid, Posizolid, Radezolid, and Torezolid. Oxazolidonones are believed to be protein synthesis inhibitors.

Penicillins include, but are not limited to, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin and Ticarcillin. Penicillins are effective, e.g., against Gram-positive bacteria, facultative anaerobes, e.g., *Streptococcus, Borrelia*, and *Treponema*. Penicillins are believed to inhibit bacterial cell wall synthesis by disrupting synthesis of the peptidoglycan layer of bacterial cell walls.

Penicillin combinations include, but are not limited to, Amoxicillin/clavulanate, Ampicillin/sulbactam, Piperacillin/tazobactam, and Ticarcillin/clavulanate.

Polypeptide antibiotics include, but are not limited to, Bacitracin, Colistin, and Polymyxin B and E. Polypeptide Antibiotics are effective, e.g., against Gram-negative bacteria. Certain polypeptide antibiotics are believed to inhibit isoprenyl pyrophosphate involved in synthesis of the peptidoglycan layer of bacterial cell walls, while others destabilize the bacterial outer membrane by displacing bacterial counter-ions.

Quinolones and Fluoroquinolone include, but are not limited to, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, and Temafloxacin. Quinolones/Fluoroquinolone are effective, e.g., against *Streptococcus* and *Neisseria*. Quinolones/Fluoroquinolone are believed to inhibit the bacterial DNA gyrase or topoisomerase IV, thereby inhibiting DNA replication and transcription.

Sulfonamides include, but are not limited to, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole), and Sulfonamidochrysoidine. Sulfonamides are believed to inhibit folate synthesis by competitive inhibition of dihydropteroate synthetase, thereby inhibiting nucleic acid synthesis.

Tetracyclines include, but are not limited to, Demeclocycline, Doxycycline, Minocycline, Oxytetracycline, and Tetracycline. Tetracyclines are effective, e.g., against Gram-negative bacteria. Tetracyclines are believed to bind to the bacterial 30S ribosomal subunit thereby inhibiting bacterial protein synthesis.

Anti-mycobacterial compounds include, but are not limited to, Clofazimine, Dapsone, Capreomycin, Cycloserine, Ethambutol, Ethionamide, Isoniazid, Pyrazinamide, Rifampicin, Rifabutin, Rifapentine, and Streptomycin.

Suitable antibiotics also include arsphenamine, chloramphenicol, fosfomycin, fusidic acid, metronidazole, mupirocin, platensimycin, quinupristin/dalfopristin, tigecycline, tinidazole, trimethoprim amoxicillin/clavulanate, ampicillin/sulbactam, amphomycin ristocetin, azithromycin, bacitracin, buforin II, carbomycin, cecropin Pl, clarithromycin, erythromycins, furazolidone, fusidic acid, Na fusidate, gramicidin, imipenem, indolicidin, josamycin, magainan II, metronidazole, nitroimidazoles, mikamycin, mutacin B-Ny266, mutacin B-JH1 140, mutacin J-T8, nisin, nisin A, novobiocin, oleandomycin, ostreogrycin, piperacillin/tazobactam, pristinamycin, ramoplanin, ranalexin, reuterin, rifaximin, rosamicin, rosaramicin, spectinomycin, spiramycin, staphylomycin, streptogramin, streptogramin A, synergistin, taurolidine, teicoplanin, telithromycin, ticarcillin/clavulanic acid, triacetyloleandomycin, tylosin, tyrocidin, tyrothricin, vancomycin, vemamycin, and virginiamycin.

In some embodiments, the the cancer therapy comprises administering a therapeutic bacteria and/or a therapeutic combination of bacteria to the subject so a healthy microbiome can be reconstituted in the subject. In some embodiments, the therapeutic bacteria is a non-cancer-associated bacteria. In some embodiments the therapeutic bacteria is a probiotic bacteria.

Cancer

In some embodiments, the methods and compositions described herein relate to the treatment of cancer. Examples of cancers that may treated by methods described herein include, but are not limited to, hematological malignancy, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, rhabdosarcoma, serocystic sarcoma, synovial sarcoma, telangiectaltic sarcoma, Hodgkin's Disease, Non-Hodgkin's Lymphoma, multiple myeloma, neuroblastoma, bladder cancer, breast cancer, ovarian cancer, lung cancer, colorectal cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, superficial spreading melanoma, plasmacytoma, colorectal cancer, rectal cancer.

In some embodiments, the methods and compositions provided herein relate to the treatment of a leukemia. The term "leukemia" is meant broadly progressive, malignant diseases of the hematopoietic organs/systems and is generally characterized by a distorted proliferation and development of leukocytes and their precursors in the blood and bone marrow. Non-limiting examples of leukemia diseases include, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemia.

In some embodiments, the methods and compositions provided herein relate to the treatment of a carcinoma. The term "carcinoma" refers to a malignant growth made up of epithelial cells tending to infiltrate the surrounding tissues, and/or resist physiological and non-physiological cell death signals and gives rise to metastases. Non-limiting exemplary types of carcinomas include, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, merkel cell carcinoma, and salivary gland carcinoma.

In some embodiments, the methods and compositions provided herein relate to the treatment of a sarcoma. The term "sarcoma" generally refers to a tumor which is made up of a substance like the embryonic connective tissue and is generally composed of closely packed cells embedded in a fibrillar, heterogeneous, or homogeneous substance. Sarcomas include, but are not limited to, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Additional exemplary neoplasias that can be treated using the methods and compositions described herein include Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some embodiments, the cancer treated is a melanoma. The term "melanoma" is taken to mean a tumor arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

Particular categories of tumors that can be treated using methods and compositions described herein include lymphoproliferative disorders, breast cancer, ovarian cancer, prostate cancer, cervical cancer, endometrial cancer, bone cancer, liver cancer, stomach cancer, colon cancer, colorectal cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

Cancers treated in certain embodiments also include pre-cancerous lesions, e.g., actinic keratosis (solar keratosis), moles (dysplastic nevi), acitinic chelitis (farmer's lip), cutaneous horns, Barrett's esophagus, atrophic gastritis, dyskeratosis congenita, sideropenic dysphagia, lichen planus, oral submucous fibrosis, actinic (solar) elastosis and cervical dysplasia.

Cancers treated in some embodiments include non-cancerous or benign tumors, e.g., of endodermal, ectodermal or mesenchymal origin, including, but not limited to cholangioma, colonic polyp, adenoma, papilloma, cystadenoma, liver cell adenoma, hydatidiform mole, renal tubular adenoma, squamous cell papilloma, gastric polyp, hemangioma, osteoma, chondroma, lipoma, fibroma, lymphangioma, leiomyoma, rhabdomyoma, astrocytoma, nevus, meningioma, and ganglioneuroma.

EXAMPLES

Example 1: Culture of *Blautia massiliensis* Strain A on Selective Media

Required Equipment:
Anaerobic chamber (10% H2, 5% CO2, 85% N2 atmosphere at 35-370C)
Multi sample vortex
100 uL pipettor
 Consumables:
Sterile loops
Colony spreader
Pipets
Pipet tips
96-well sterile plates
96-well deep-well plates
 Media:

source. Sodium Pyruvate is added as an energy source and as an oxygen scavenger for asaccharolytic cocci, including *Veillonella* spp. L-Cysteine HCl.H20 is a reducing agent and growth stimulant for anaerobes. L-Arginine is added to ensure the growth of *Eubacterium* lentum, and Hemin and Vitamin K are growth factors required by several *Bacteroides* spp. Sodium Succinate improves the growth of *Prevotella melaninogenica* and *Bacteroides* spp.

Anaerobe Basal Agar. (Oxoid CM0972)

Anaerobe Basal Agar contains peptones, carefully selected to support good growth of anaerobic bacteria and yeast extract as a vitamin source. Starch is present to absorb any toxic metabolites1. Sufficient arginine is added to ensure the growth of *Eubacterium*, lentum, hemin and vitamin K are growth factors required by many *Bacteroides* species. Hemin is also required by *Porphyromonas* species. Sodium succinate improves the growth of *Prevotella, melaninogenica* and *Bacteroides* species4. Sodium pyruvate is added as an energy source for asaccharolytic cocci such as *Veillonella*. It also acts similarly to catalase and degrades traces of hydrogen peroxide, which may be produced by the action of molecular oxygen on media components5. L-cysteine hydrochloride and dithiothreitol are reducing agents, and cysteine has also been shown to stimulate the growth of some anaerobes

TABLE 1

Media preparation sheet.

| Component | Conc./L | Amount Added | Brand | Catalog # | Lot # | Expiration Date |
|---|---|---|---|---|---|---|
| 1. Fastidious anaerobes agar (FAA)powder | — | 45.7 g/L | Acumedia | — | 107852B | Jul. 31, 2019 |
| +Yeast extract(granulated) | 5 g/L | 5 g/L | Fisher bioreagents | — | 146772 | August 2017 |
| +Erythromycin to make (FAA + Ery) | 32 ug/L | 1 mL/1 L | MP Biomedicals | 190197 | M9033 | January 2017 |
| +Ciprofloxacin to make (FAA + Cipro) | 16 ug/L | 1 mL/1 L | Sigma | 449620050 | A0355311 | N/A |
| +Ampicillin to make (FAA + Ampi) | 50 ug/L | 1 mL/1 L | Fisher Scientific | 69523, BP1760-25 | 151231 | N/A |
| +Tetracycline to make (FAA + TET) | 16000 ug/L | 1 mL/1 L | Fisher | 64755 | 152874 | N/A |
| 2. GAM broth with agar | GAM broth with1.5% agar | 59 g/L | HIMEDIA/Fisher | M1801/BP1423 | N/A | N/A |
| 3. Anaerobe Basal Agar. | — | 46 g/L | Oxoid | CM0972 | N/A | N/A |

Fastidious anaerobic agar (FAAy) (Acumedia7531A) with Antibiotics. Selective media prepared at Epiva.

These antibiotics are added to the media in order to inhibit the growth of other group of bacteria that might interfere with the isolation of Blautia.
FAA+50 ug/ml Ampicillin
FAA+16 ug/ml Erythromycin
FAA+16 ug/ml Ciprofloxacin
FAA+32 ug/ml TetracyclineFastidious Anaerobe Agar is a custom formulation used for the cultivation of various fastidious anaerobes from clinical and nonclinical specimens. Peptone provides nitrogen and vitamin sources in Fastidious Anaerobe Agar. Sodium Chloride maintains the osmotic balance of the medium. Soluble Starch is present to absorb any toxic metabolites. Sodium Bicarbonate increases the aerotolerance by acting as an oxygen scavenger. Sodium Pyrophosphate is a buffering agent. Glucose is the carbon Gifu Anaerobic Medium (GAM Broth) (HIMEDIA M1801) Agar (FisherBP1423)

This is a liquid medium for anaerobic bacteria. As this medium contains the digested serum which has hemin, serves as essential growth factor and Sodium chloride maintains osmotic equilibrium. Also contains Sodium thioglycolate and L-Cysteine are the reducing agents added in this medium to provide adequate anaerobiosis. Peptic digest of animal tissue and yeast extract provide nitrogen, carbon and vitamin source. Starch absorbs the toxic metabolites produced. Anaerobic organisms require reducing condition and an absence of dissolved oxygen in the medium. Strict anaerobes obtain its energy and intermediates through oxidation utilizing hydrogen acceptors other than oxygen.

Peptone Yeast (PY)(AS-821) with: Glycogen, N-Acetil-D-Glucosamine, Cellulobiose.

PRAS (Pre-reduced Anaerobically Sterilized) Peptone Yeast Extract Broth Based Media (PY) are enriched non-selective broth media used in the growth and partial identification of anaerobic bacteria. Peptone Yeast Extract Broth Based Media with carbohydrate/biochemical additives are designed for determination of specific biochemical features of anaerobic bacteria. This biochemical determination is used to aid in the definitive identification of anaerobic bacteria. Peptone Yeast Extract Broth Based Media are enriched non-selective media that are supplemented with hemin and vitamin K1 to facilitate the recovery of the more fastidious organisms such as *Prevotella, Porphyromonas* and the *Bacteroides fragilis* group. Resazurin is added as a redox indicator. PRAS biochemicals are considered to be the "gold standard" for biochemical testing and characterization of anaerobes. With the addition of a specific biochemical, the Peptone Yeast Extract Broth Based Media are used to determine whether anaerobic bacteria will utilize the biochemical or if growth is stimulated or inhibited by the biochemical.

Procedure

Step 1. Recovery of Bacteria from Frozen Stool Samples.

Frozen stool sample is transferred to the anaerobic chamber to work with.

The sample that is left on a swab is placed onto a new sterile transport media for storage at −80C freezer as soon as possible to preserve the sample for further applications.

2.5 ml of sterile Phosphate Buffered Saline (PBS) is added in the transport media (original sample) containing the rest of the stool sample. The mixture is mixed very well, vortexed gently if required 1 ml aliquot is remove and added to a tube containing 9 mL of sterile Phosphate Buffered Saline (PBS) resulting (1:10 dilution). The mixture is vortexed gently. The remaining sample is frozen at −80C.

1 mL from 1:10 ($10^{-1}$) is transferred into a 9 mL tube of PBS resulting in 1:100 (10-2). Continue the serial dilution to reach a dilution of $10^{-5}$ Step 2. Enumeration of Solid Media.

The following agar plates are labeled with the subject information and dilution factor:

GAM with Agar,
Anaerobic Basal Agar,
FAA+50 ug/ml Ampicillin,
FAA+32 ug/ml Erythromycin,
FAA+16 ug/ml Ciprofloxacin,
FAA+16 ug/ml Tetracycline,
PY-glycogen,
PY-N-Acetil-D-Glucosamine,
PY-Cellobiose 100 uL aliquots of dilutions $10^{-3}$, $10^{-4}$, $10^{-5}$ is transferred in onto the surface of the agar plates. This results in a final dilution range of $10^{-4}$, $10^{-5}$ and $10^{-6}$ CFU/ml of stool.

One of each plate is labeled NEGATIVE Control. 100 uL of sterile PBS is transferred on to surface of plate. This is to verify the sterility of PBS, media plates and colony spreader at the time of use.

After plating, diluted samples are stored at RT.

A colony spreader is used to spread aliquot evenly across surface of agar. Plates are allowed to seat for approximately 10 min (or until dry) to allow spread inoculum to absorb into the plates.

Inverted plates are incubated in the anaerobic chamber at 37° C. for 48-72 hours (or until colonies are visible up to 5 days).

plates are checked based on colony morphology pick 3 isolated colonies of the same morphology for PCR and re-isolate them on BHI, or CDC blood agar plates to perform further testing and/or isolate single colonies from a pure culture for PCR.

Colonies are picked using either sterile disposable loops or pipette tips, and diluted in 100 μL distilled water (easiest to do this in a 96-well plate).

These suspensions are then cycled outside of the chamber, while the plates remain for downstream recovery of strains of interest.

PCR is performed using the following reaction mixture (in a 96-well PCR plate):

a-12.5 μL Go Taq Green Master Mix (Promega, cat # M7123)

```
b-0.2 µL 16S rDNA primer 27F
  (5' AGAGTTTGATCMTGGCTCAG 3' (SEQ ID NO: 1))

c-0.2 µL 16S rDNA primer 1492R
  (5' TACGGYTACCTTGTTACGACTT 3 (SEQ ID NO: 2))
``` d-11.1 μL nuclease free distilled water (sent with the master mix)

e-1 μL diluted cell inoculum

PCR protocol is as follows . . .

a. 10-minute denaturation at 95° C.
b. 30 seconds at 95° C.
c. 30 seconds at 59° C.
d. 30 seconds at 72° C.
e. (repeated b-d 30 times)
f. 5 minutes at 72° C.
g. Hold at 4° C.

Successful PCR is confirmed on 18 reactions using gel electrophoresis. If over 60% success, 96-well plate of PCRs is sent to Genewiz for sequencing. Isolated colonies confirmed by PCR are grown in liquid culture, and cryopreserved as described above. Pictures of colony morphology and Gram stain are taken using microscope (100× magnification). If multiple isolates are identified, bacteria are grown and stored in 96 deep-well plates.

Example 2: *Blautia Massiliensis* Strain A Production

Enriched media is used to grow and prepare *Blautia massiliensis* for in vitro and in vivo use. For example, media may contain sugar, yeast extracts, peptones, trace elements, and vitamins. Alternatively, media may be prepared and *Blautia massiliensis* grown as is known in the art. Influence of fermentation time, cryoprotectant and neutralization of cell concentrate on freeze-drying survival, storage stability, and acid and bile exposure of *Blautia massiliensis* cells produced without milk-based ingredients, At large scale, the media is sterilized. Sterilization may be by Ultra High Temperature (UHT) processing. The UHT processing is performed at very high temperature for short periods of time. The UHT range may be from 135-180° C. For example, the medium may be sterilized from between 10 to 30 seconds at 135° C.

Inoculum can be prepared in flasks or in smaller bioreactors and growth is monitored. For example, the inoculum size may be between approximately 0.5 and 3% of the total bioreactor volume. Depending on the application and need for material, bioreactor volume can be at least 2 L, 10 L, 80 L, 100 L, 250 L, 1000 L, 2500 L, 5000 L, 10,000 L.

Before the inoculation, the bioreactor is prepared and ready with medium at desired pH, temperature, and oxygen concentration. For example, pH may be set between 4.5 and 8.0 During the fermentation the pH can be controlled through the use of sodium hydroxide, potassium hydroxide, or ammonium hydroxide. The temperature may be controlled from 25° C. to 45° C., for example at 37° C. Anaerobic conditions are created by reducing the level of oxygen in the culture broth from around 8 mg/L to 0 mg/L. For example, nitrogen or gas mixtures ($N_2$, $CO_2$, and $H_2$) may be used in order to establish anaerobic conditions. Alternatively, no gases are used and anaerobic conditions are established by cells consuming remaining oxygen from the medium. Depending on strain and inoculum size, the bioreactor fermentation time can vary. For example, fermentation time can vary from approximately 5 hours to 48 hours.

Harvesting can be performed by continuous centrifugation. Product will be resuspended with various excipients to a desired final concentration. Excipients can be added for cryo protection or for protection during lyophilization. Excipients can include, but are not limited to, sucrose, trehalose, or lactose, and these may be alternatively mixed with buffer and antioxidants. Prior to lyophilization, droplets of cell pellets mixed with excipients are submerged in liquid nitrogen.

Lyophilization of material, including live bacteria, begins with primary drying. During the primary drying phase, the ice is removed. Here, a vacuum is generated and an appropriate amount of heat is supplied to the material for the ice to sublime. During the secondary drying phase, product bound water molecules are removed. Here, the temperature is raised higher than in the primary drying phase to break any physico-chemical interactions that have formed between the water molecules and the product material. The pressure may also be lowered further to enhance desorption during this stage. After the freeze-drying process is complete, the chamber may be filled with an inert gas, such as nitrogen. The product may be sealed within the freeze dryer under dry conditions, preventing exposure to atmospheric water and contaminants.

Example 3: *Blautia Massiliensis* Strain A Fermentation Process

TSBF Preparation:

TABLE 2

| Group 1 components | |
| --- | --- |
| Group 1 | g/L |
| Yeast Extract 19512 Organotechnie S.A.S. | 10 |
| Soy Peptone E110 19885 Organotechnie S.A.S | 10 |
| Soy Peptone A2 SC 19649 Organotechnie S.A.S | 10 |
| Potato Peptone E210 19425 Organotechnie S.A.S | 5 |
| Dipotassium Phosphate $K_2HPO_4$ | 2.5 |
| Sodium Chloride | 5 |

Group 1 components are combined in appropriate volume of DI water, remembering to multiply 1 L by the number of liters desired. The mixture is then autoclave for 60 minutes with a maximum volume in each container of 2.5 L.
Group 2 components: L-Cysteine-HCl (50 g/L) and $FeSO_4$ (5 g/L)

Group 2 components are combined with appropriate volume of DI water. The mixture is aliquoted into 100 mL volumes in 200 mL bottles. Rubber stoppers and crimp metal cap are inserted. The mixture is then autoclaved for 30 minutes.

Glucose

There are two (2) types of glucose stocks. One is the pre-sterilized 45% glucose solutions from Sigma Aldrich (use 11.1 ml/L). The other is the 50% filter sterilized stocks made in-house (use 10.0 ml/L).

To make 50% stocks, 1 L of DI water is heated in microwave for 2.5 minutes. 400 mL of heated water was stirred vigorously while slowly adding 500 g of glucose, not allowing glucose to clump in solution. After all glucose is dissolved, solution is allowed to continue mixing while heating on stir plate for 5 minutes. Hot DI water is then added up to 1 L volume. The mixture is filtered sterilize using 0.2 um vacuum filter. 5 g/L is the concentration of glucose in the final medium.

Combination: 10 mL of Group 2 is added for every liter of Group 1. Appropriate volume of glucose stock solution is then added.

Objective: To investigate the influence of pH and alternative cryoprotectants on growth and stability of *Blautia massiliensis* strain A. To observe the correlation between CFU and GDA as well as the variance between these methods of analysis. GDA data are used to find an acceptable dilution that allows high resolution and comparison between GDA and CFU. D002 are also used to test changes to pH control PID. Finally, procedures and run-sheets are changed based upon improvements made during D002. Downsteam sampling is performed with 4 different stabilizers and one control.

Procedures: The following procedures were used to setup and execute DasGip fermentation run D002. See the procedure archive for the materials and methods associated with each listed procedure.

DasGip Setup Laboratory Procedure v0.1
Anaerobic Inoculum Preparation Laboratory Procedure v0.1
Bioreactor Inoculation Laboratory Procedure v0.1
DasGip Sampling and Analysis Laboratory Procedure v0.1
Colony Forming Units Laboratory Procedure v0.1
Optical Density and Growth Detection Assay Laboratory procedure v0.1

Methods: Select methods and parameters are described below as well as any methods not included in the procedures above and/or deviating from the noted procedures.

Media: Media used for fermentation and inoculum was prepared per Base Medium "BM1" Media Prep. Formulation v0.1. The following batch(s) was used: BM109271601. Media was added to each vessel under sterile conditions in a biosafety cabinet. pH adjustments were performed using the DasGip controller (10N NaOH). Media was de-gassed overnight to under mixed gas sparging (5% H2, 5% CO2, Balance N2) prior to inoculation. 10 ppm of sterile Antifoam Emulsion C was added via sterile syringe after de-gassing.

Calibrations: Calibrations of pH and RD probes were performed prior to autoclaving of the vessels. A clean in place procedure was performed on pump "B" prior to connecting base lines to each vessel. Calibration values and probe serial numbers are listed below.

TABLE 3

| | Unit 1 | Unit 2 | Unit 3 | Unit 4 |
| --- | --- | --- | --- | --- |
| pH Probes: Hamilton Easy Ferm Plus K8 200 | | | | |
| S/N | 18533 | 18380 | 18560 | 18562 |
| Offset | 0.061 | −0.029 | 0.038 | 0.02 |
| Slope | 99.10% | 97.55% | 97.55% | 97.97% |
| RD Probes: Mettler Toledo Pt4805-SC-DPAS-K8S/225 | | | | |
| S/N | 5501480 | 5482413 | 5482414 | N/A |
| Offset | 5.048 | 7.665 | 8.803 | N/A |

Headplate/Tubing: The vessel headplate and tubing was prepared, cleaned and inspected prior to the run. All luer valves were replaced from the previous run.

Autoclaving/Setup: The vessels were autoclaved per the setup procedure, each containing 300 mL of 1×PBS which was decanted prior to filling with media. Bottles for base were prepared, 1 bottle for each vessel. Bottles were filled in the biosafety cabinet with 10N sodium hydroxide, however, the sodium hydroxide was not sterile filtered due to the viscosity. All lines were connected, and control loops initialized prior to inoculation. All process parameters were allowed to reach equilibrium prior to inoculation.

Inoculum: The inoculating culture (*Blautia massiliensis* strain A) for D002 was prepared, in BM1 media, and grew for 12 hours. Then, 10 mL of the culture was added to each vessel. The OD of the inoculating culture was 0.658. Result of inoculum growth were recorded in the strain bank master file. The pH of all vessels was approx. 7.00 at the time of inoculation.

Process Parameters: The following process parameters were used during the run.
Parameters were not changed after inoculation.
Temperature: 37C
Sparger Flow: 145 mL/min
Overlay Flow: 85 mL/min
Agitation: 150 RPM
pH:
Vessel 1: 5.20
Vessel 2: 5.80
Vessel 3: 6.40
Vessel 4: 7.00

The details about the process are below.
pH control at 7.0
Temperature 37 C
Inoculum size 1%
Gas 90% N2+5% CO2
Sparging 0.1 vvm
Agitation 300 rpm Sampling and Analysis: Sampling and Analysis was performed. An additional five vacutainer samples were taken from each vessel during samples 1 and 3 to be used for downstream analysis. Ten additional vacutainer samples were taken from each vessel during sample 2 for the same purpose. A vacutainer sample was taken from each vessel immediately prior to takedown for quality control analysis via 16S PCR. Sampling times are listed in Table 4 below.

TABLE 4

Sampling

| Time | Run Time (DD:HH:MM) | Sample | Vessel | PVs OK? | Notes |
|---|---|---|---|---|---|
| 8:30 | 00:11:47 | 1 | 1, 2, 3, 4 | OK | |
| 12:41 | 00:15:15 | 2 | 1, 2, 3, 4 | OK | |
| 15:36 | 00:18:11 | 3 | 1, 2, 3, 4 | OK | |

Reactor Takedown: The run was stopped a day later and all takedown procedures performed.

Critical Process Parameters: D002 passes all critical process parameter checks.

Data: A selection of data is reproduced in its un-manipulated form below for ease of reference.

TABLE 5

CFU

| Sample | Vessel | CFU av (cell/mL) | SD | RSD (%) | Note* |
|---|---|---|---|---|---|
| 1 | 1 | 2.97E+09 | 8.02E+08 | 27.03642565 | |
| | 2 | 4.10E+09 | 5.29E+08 | 12.90610396 | |
| | 3 | 4.90E+09 | 4.58E+08 | 9.352195296 | |
| | 4 | 2.60E+09 | 4.58E+08 | 17.62529113 | |
| 2 | 1 | 2.33E+08 | 1.15E+08 | 49.48716593 | |
| | 2 | 7.33E+08 | 3.51E+08 | 47.88933524 | |
| | 3 | 4.33E+08 | 5.77E+07 | 13.32346775 | |
| | 4 | 9.67E+08 | 3.51E+08 | 36.32984053 | |
| 3 | 1 | 1.30E+09 | 5.20E+08 | 39.97040325 | |
| | 2 | 3.60E+09 | 4.00E+08 | 11.11111111 | |
| | 3 | 1.90E+09 | 2.65E+08 | 13.9250069 | |
| | 4 | 2.53E+09 | 4.04E+08 | 15.95309954 | |

TABLE 6

Optical Density

| Sample | Vessel | Dilution | Average | Stdev | Note* |
|---|---|---|---|---|---|
| 1 | 1 | 20x | 5.18 | 0.03 | |
| | 2 | 20x | 5.98 | 0.07 | |
| | 3 | 20x | 5.57 | 0.11 | |
| | 4 | 20x | 5.51 | 0.01 | |
| 2 | 1 | 20x | 6.96 | 0.05 | |
| | 2 | 20x | 5.59 | 0.06 | |
| | 3 | 20x | 6.62 | 0.05 | |
| | 4 | 20x | 6.97 | 0.17 | |
| 3 | 1 | 20x | 6.37 | 0.09 | |
| | 2 | 20x | 5.36 | 0.03 | |
| | 3 | 20x | 6.44 | 0.14 | |
| | 4 | 20x | 6.81 | 0.14 | |

Figure 9:
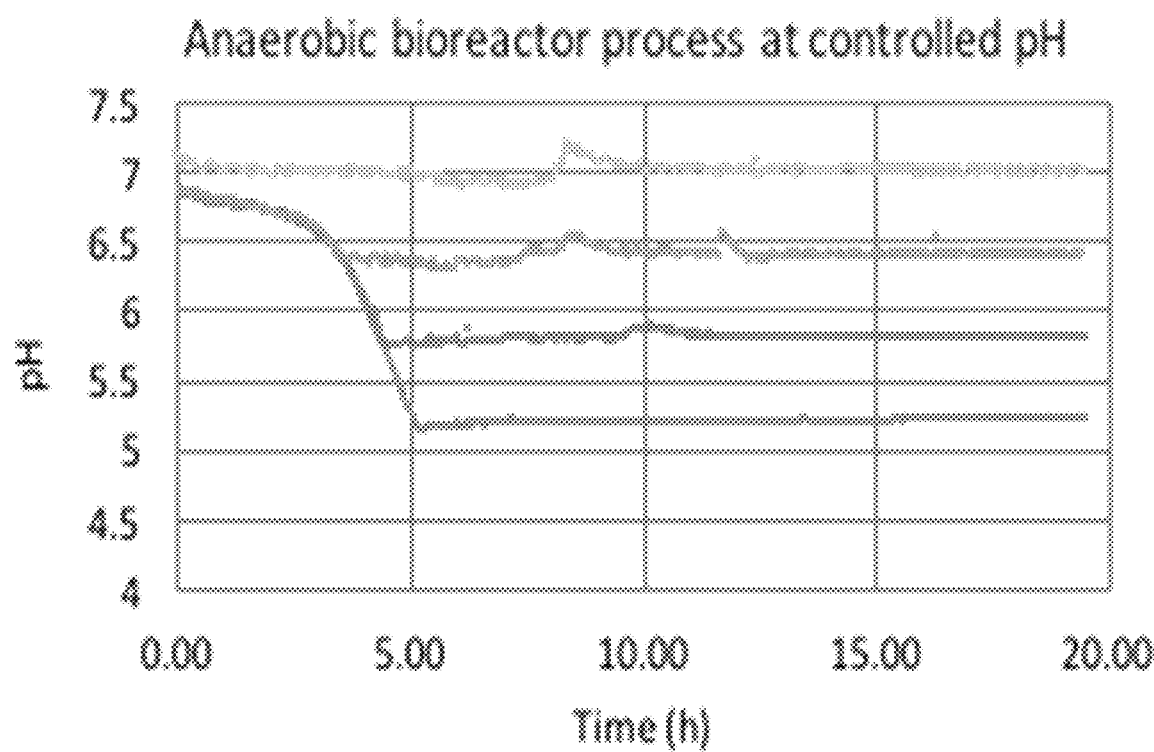
FIG. 9 shows anaerobic bioreactor process at controlled pH at different set points.
Figure 10:
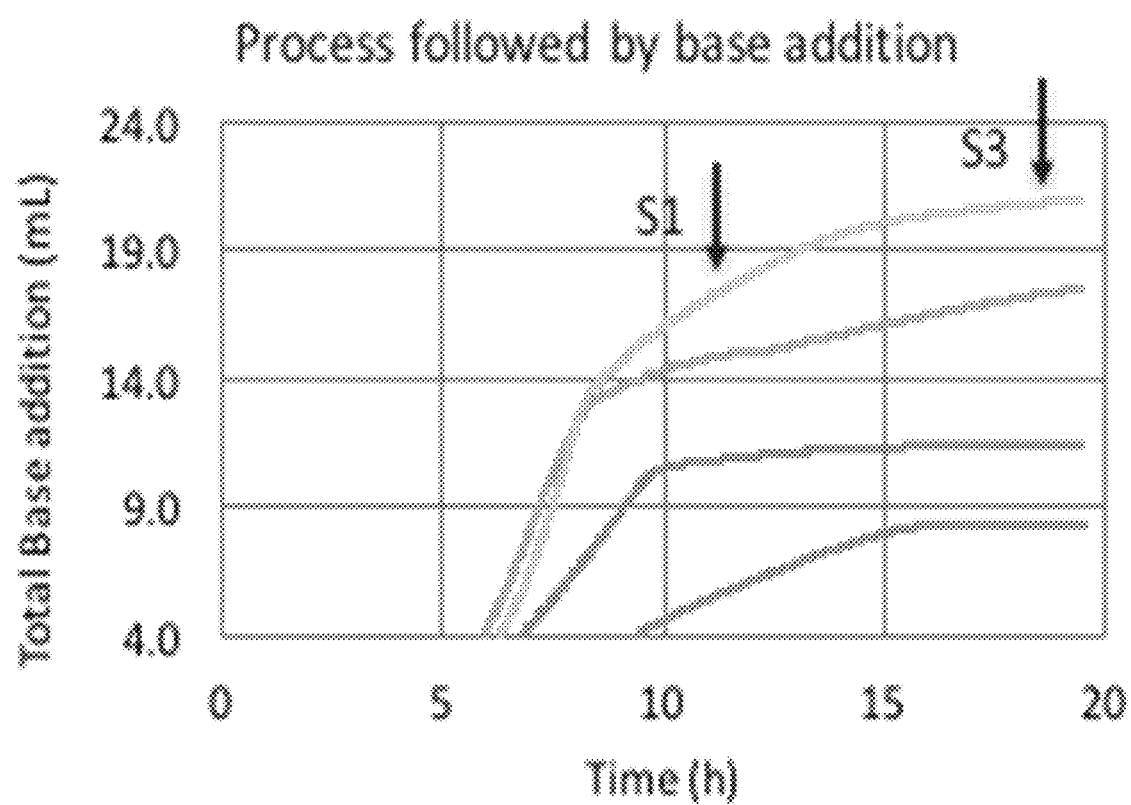
FIG. 10 shows total base addition during fermentation processes; samples S1 and S3 were taken at designated points.
Figure 11:
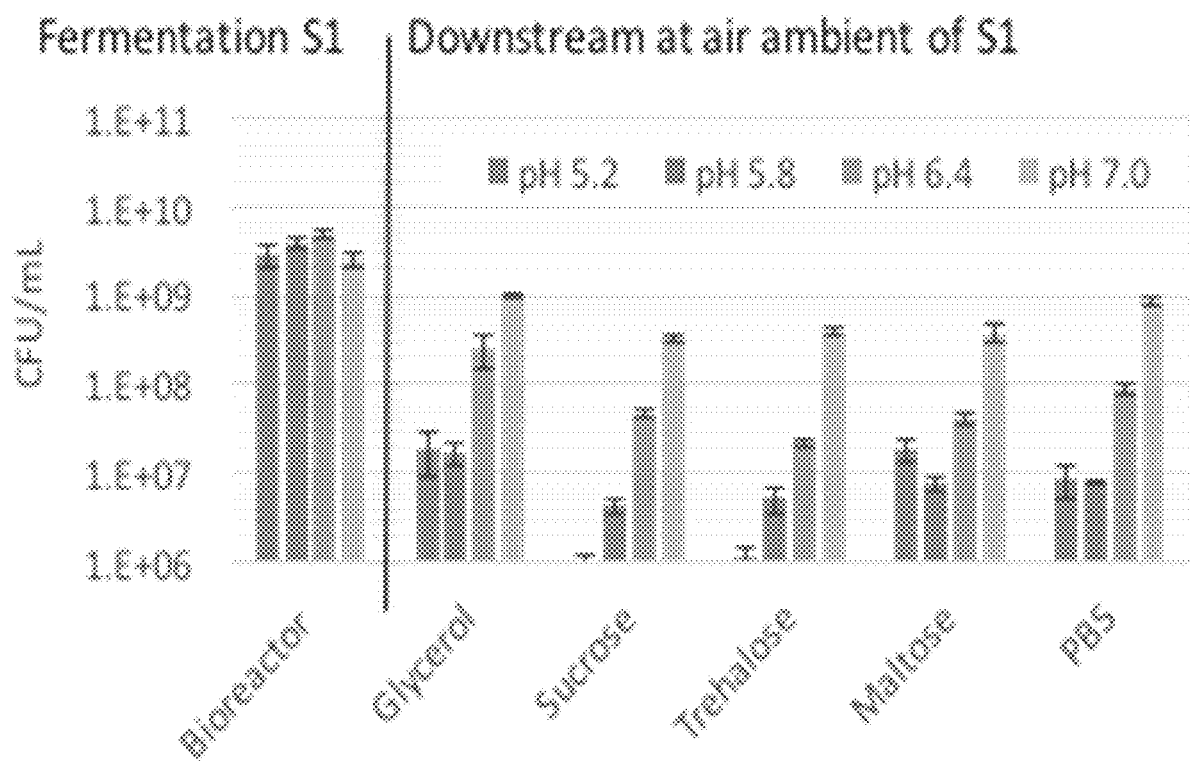
FIG. 11 shows cell recovery after downstream processing.
Figure 12:
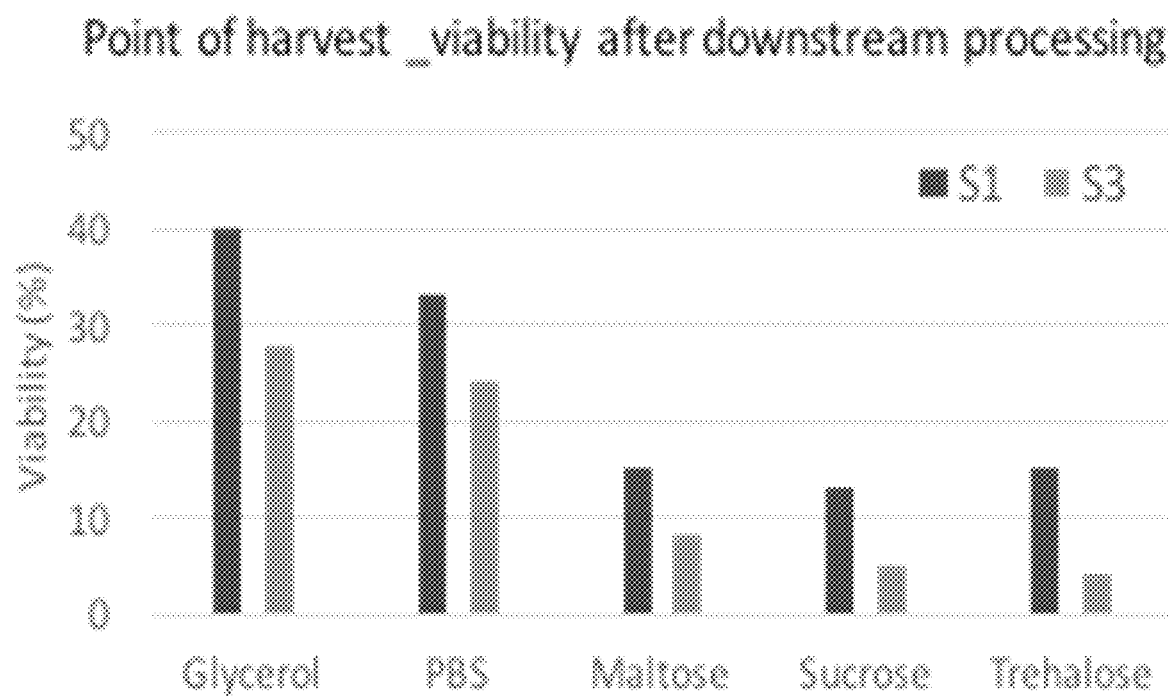
FIG. 12 shows relative cell viability of samples S1 and S3 after downstream processing.

Results:
FIG. 9 shows anaerobic bioreactor process at controlled pH at different set points. FIG. 10 shows total base addition during fermentation processes; samples S1 and S3 were taken at designated points. FIG. 11 shows cell recovery after downstream processing. FIG. 12 shows relative cell viability of samples 51 and S3 after downstream processing.

Conclusions: pH data indicates that the used PID settings provided robust control of pH in the DasGip system (FIG. 9). Total base addition in FIG. 10 may show a metabolic switch occurring as cells switch from exponential to stationary phase. bacteria grew in bioreactors up to $5 \times 10^9$ CFU per mL (FIG. 11). The growth was similar at different pH set points, however, the recovery after air ambient downstream processing was significantly influenced by bioreactor pH (FIG. 11). An early point of harvest resulted better recovery (FIG. 12).

Figure 2:
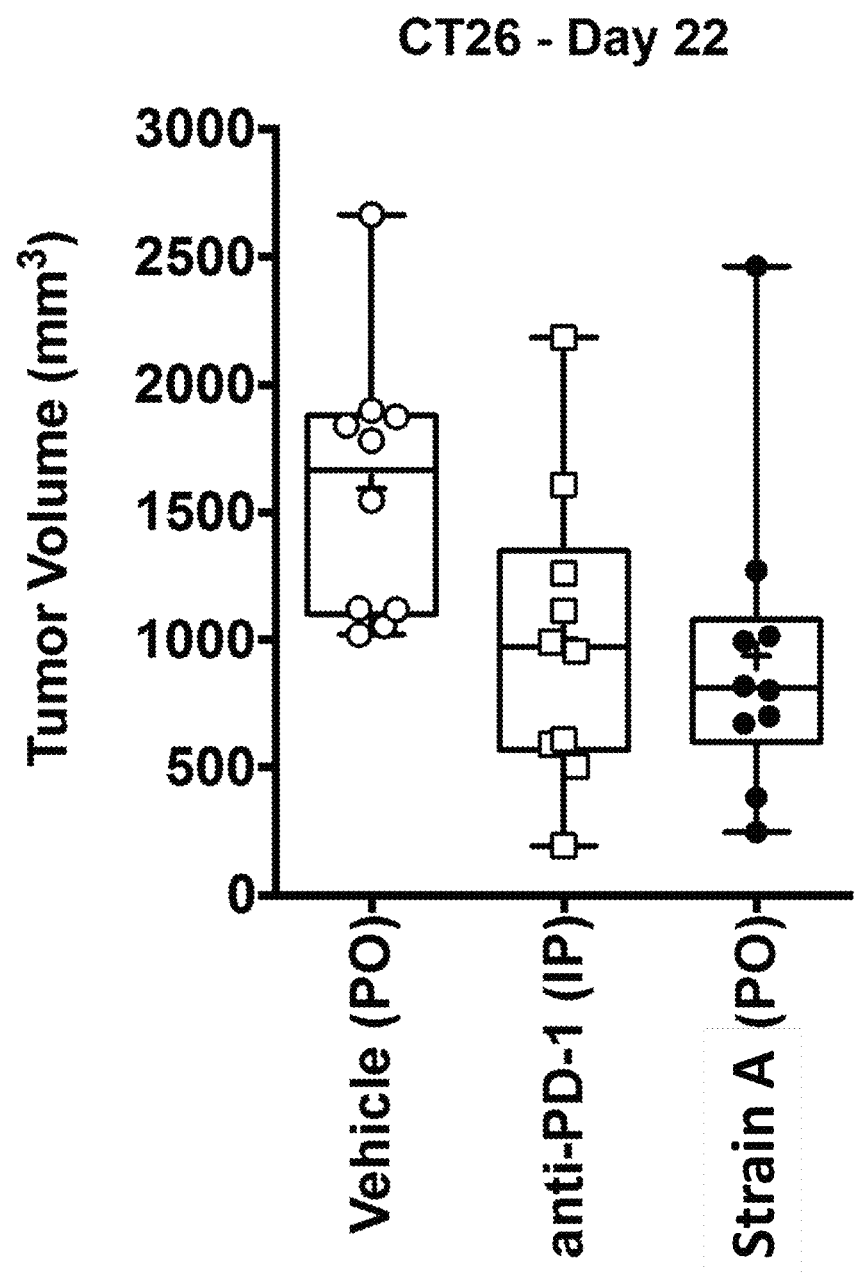
FIG. 2 shows inhibition of tumor growth (by volume) by the oral administration of *Blautia* Strain A compared to intraperitoneally (i.p.) administered anti-PD-1 in a mouse colorectal carcinoma model.

Example 4: Orally Administered *Blautia* Strain A Inhibits Colorectal Carcinoma Tumor Growth Female 6-8 week old Balb/c mice were obtained from Taconic (Germantown, N.Y.). 100,000 CT-26 colorectal tumor cells (ATCC CRL-2638) were resuspended in sterile PBS and inoculated in the presence of 50% Matrigel. CT-26 tumor cells were subcutaneously injected into one hind flank of each mouse. When tumor volumes reached an average of 100 mm$^3$ (approximately 10-12 days following tumor cell inoculation), animals were distributed into the following groups: 1) Vehicle+PBS; 2) anti-PD-1 antibody; and 3) *Blautia massiliensis* Strain A (ATCC Deposit Number PTA-125134). Antibodies were administered intraperitoneally (i.p.) at 100 ug/mouse (100 ul final volume) every four days, starting on day 1, and *Blautia* Strain A bacteria (5.5×10⁴) were administered by oral gavage (p.o.) daily, starting on day 1 until the conclusion of the study. The *Blautia* Strain A group showed tumor growth inhibition comparable to that seen in the anti-PD-1 group (FIGS. 1 and 2).

Example 5: *Blautia* Strain A in a Mouse Melanoma Model

Figure 3:
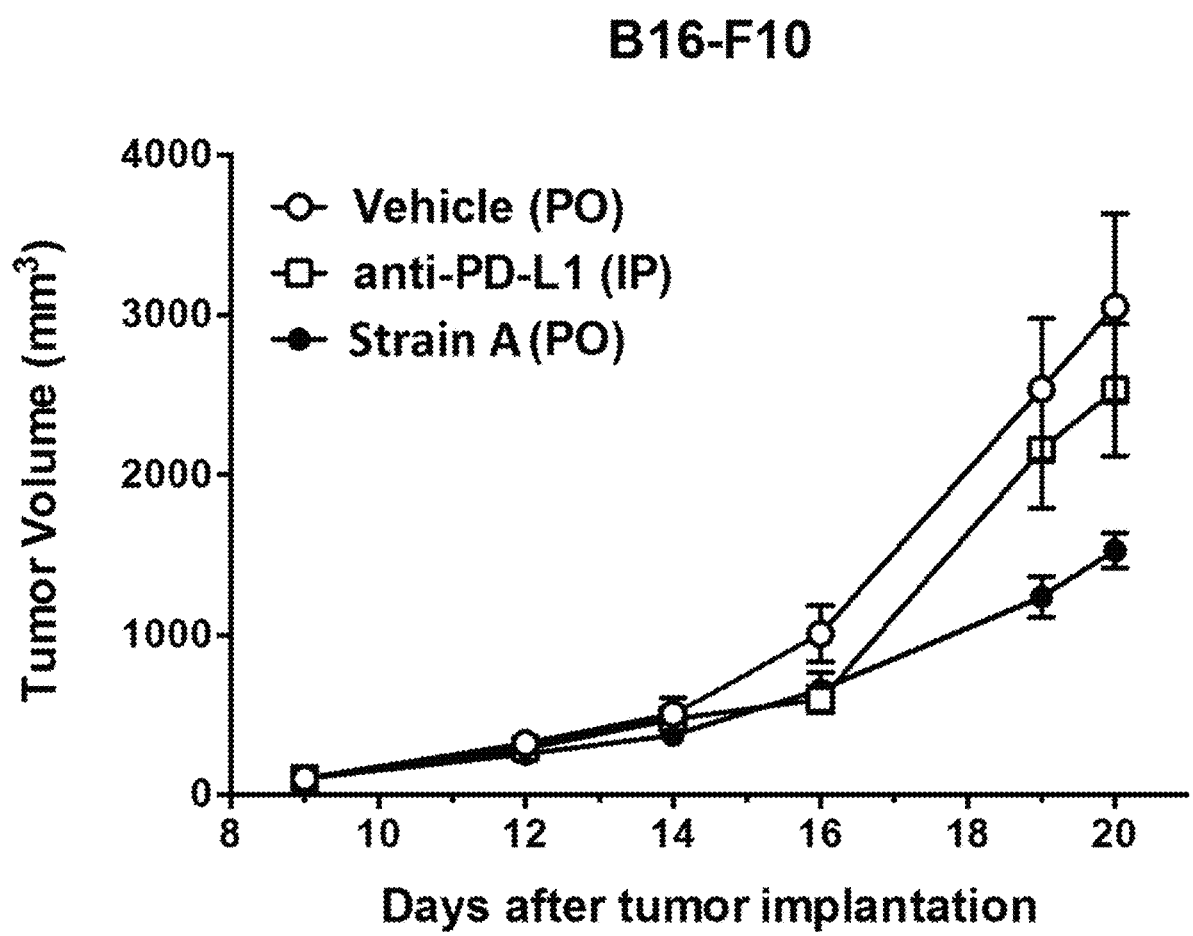
FIG. 3 shows that in a mouse melanoma model, the efficacy of orally administered *Blautia* Strain A is compared to that of intraperitoneally (i.p.) administered anti-PD-L1.
Figure 4:
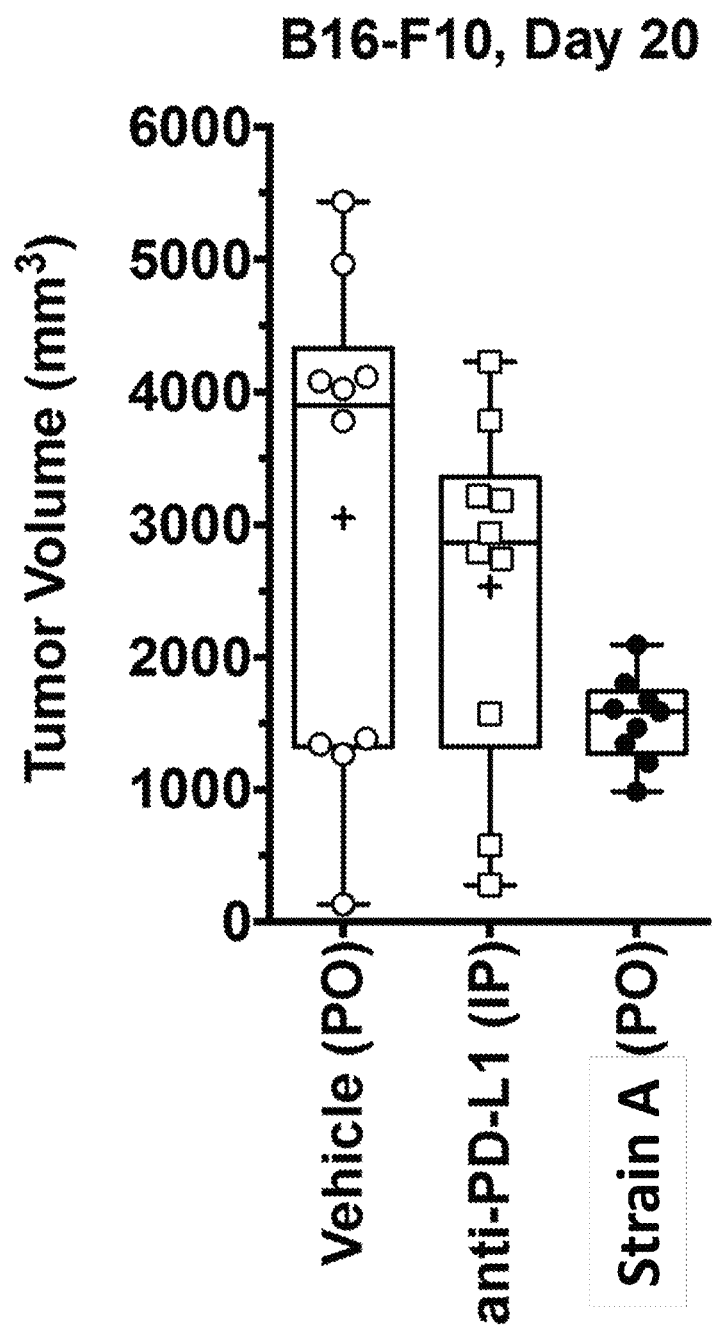
FIG. 4 shows inhibition of tumor growth (by volume) by the oral administration of *Blautia* Strain A compared to intraperitoneally (i.p.) administered anti-PD-L1 in a mouse melanoma model.

Female 6-8 week old C57Bl/6 mice were obtained from Taconic (Germantown, N.Y.). 100,000 B16-F10 (ATCC CRL-6475) tumor cells were resuspended in sterile PBS containing 50% Matrigel and inoculated in a 100 ul final volume into one hind flank (the first flank) of each mouse. Animals were distributed into the following groups: 1) Vehicle+PBS; 2) anti-PD-L1 antibody; and 3) *Blautia massiliensis* Strain A (ATCC Deposit Number PTA-125134). Antibodies were administered intraperitoneally (i.p.) at 100 ug/mouse (100 ul final volume) every four days, starting on day 1, and *Blautia* Strain A bacteria (6.1×10⁷) were administered by oral gavage (p.o.) daily, starting on day 1 until the conclusion of the study. The *Blautia* Strain A group showed better tumor growth inhibition compared to that seen in the anti-PD-L1 group (FIGS. 3 and 4).

Example 6: Treatment of Melanoma Using *Blautia massiliensis* Strain A in Combination with Anti-PD-L1

Figure 5:
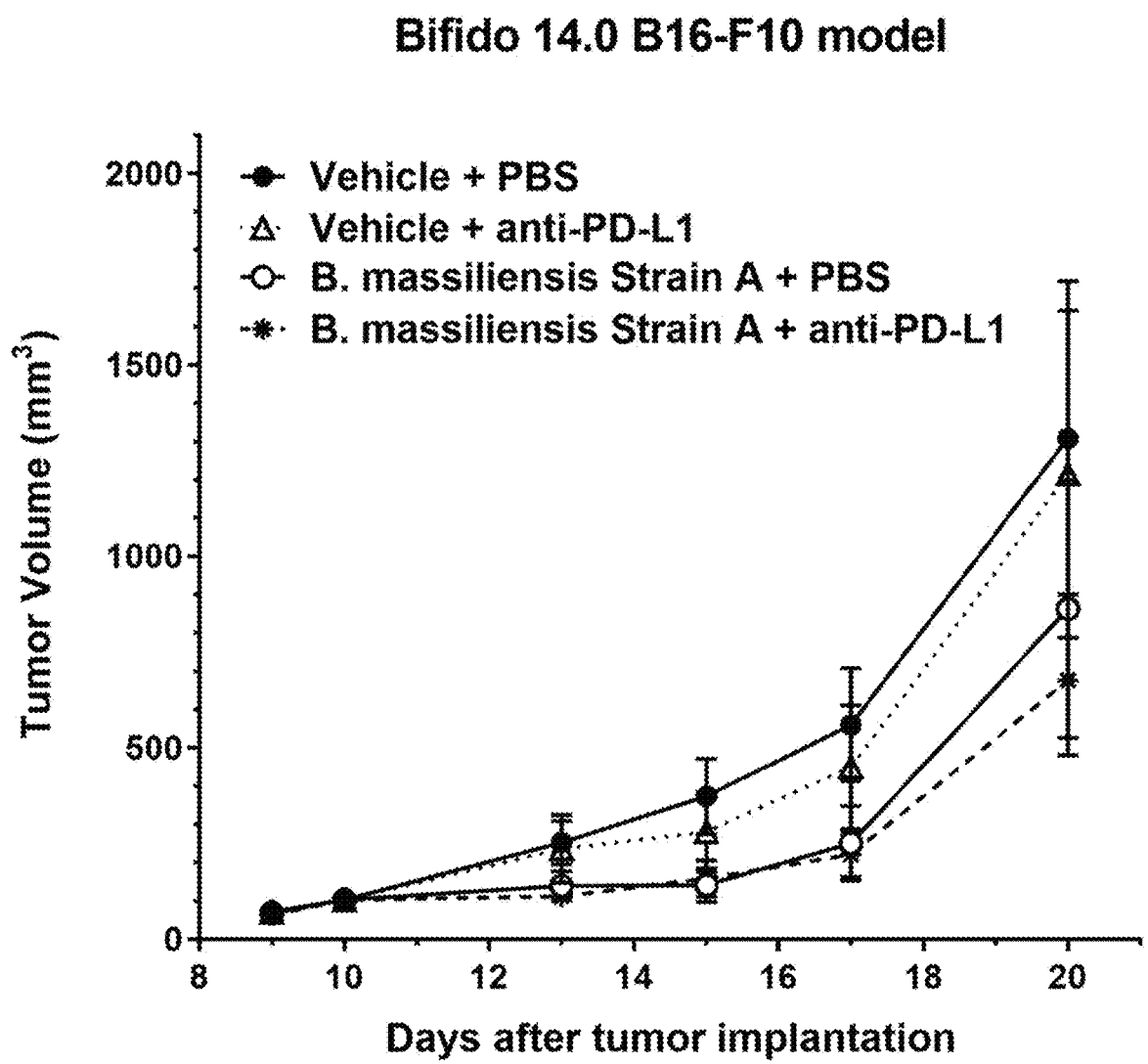
FIG. 5 shows that in a mouse melanoma model, the efficacy of administered combination therapy of *Blautia massiliensis* Strain A and anti-PD-L1.

As described in Example 5 B16-F10 (ATCC CRL-6475) tumor cells were inoculated into one hind flank (the first flank) of mice and animals were distributed into the following groups: 1) Vehicle+PBS; 2) vehicle+anti-PD-L1 antibody; 3) *Blautia massiliensis* Strain A+PBS; and 4) *Blautia massiliensis* Strain A+anti-PD-L1. Antibodies were administered intraperitoneally (i.p.) at 100 ug/mouse (100 ul final volume) every four days, starting on day 1, and *Blautia* Strain A bacteria (6.1×10⁷) were administered by oral gavage (p.o.) daily, starting on day 1 until the conclusion of the study. The *Blautia* Strain A+anti-PD-L1 group showed the best tumor growth inhibition (FIG. 5).

Example 7: Infiltration of CD3+ Cells is Significantly Increased in CT26 and B16-F10 Tumors in Mice Orally Gavaged with *Blautia massiliensis* Strain A In some studies, at various timepoints, mice are sacrificed and tumors, lymph nodes, or other tissues may be removed for ex vivo flow cytometric analysis using methods known in the art. For example, tumors are dissociated using a Miltenyi tumor dissociation enzyme cocktail according to the manufacturer's instructions. Tumor weights are recorded and tumors are chopped then placed in 15 ml tubes containing the enzyme cocktail and placed on ice. Samples are then placed on a gentle shaker at 37° C. for 45 minutes and quenched with up to 15 ml complete RPMI. Each cell suspension is strained through a 70 µm filter into a 50 ml falcon tube and centrifuged at 1000 rpm for 10 minutes. Cells are resuspended in FACS buffer and washed to remove remaining debris. If necessary, samples are strained again through a second 70 µm filter into a new tube. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1). In addition to immunophenotyping, cytokines are analyzed including, but not limited to, IP-10, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1, using techniques known in the art. Cytokine analysis may be analyzed on immune cells obtained from lymph nodes or other tissue, tumor sections, dissociated tumor cells, and/or on purified CD45+ tumor-infiltrated immune cells obtained ex vivo. Cytokine levels may be ascertained using various staining techniques, qPCR, or other techniques known in the arts. Immunohistochemistry may also be performed on tumor sections to measure T cells, macrophages, dendritic cells, and checkpoint molecule or other protein expression using techniques known in the art.

Mice were inoculated with CT26 or B16-F10 tumor cells, divided into groups as described above, and orally gavaged with *Blautia massiliensis* Strain A 8.3×10^9 CFU/mouse daily. Other mice were given vehicle as a negative control. Mice from this study were sacrificed on day 10 and tumors harvested for analysis. Using known techniques described above, tumor sections were stained with anti-CD3 antibodies (T cell marker) to assess the average CD3+ cells per tumor section, and tumor gene expression was analyzed by qPCR using a TaqMan assay as follows: Tumor RNA was isolated with Qiagen's RNeasy Mini kit (Catalog No. 74104), using the manufacturer's protocol. cDNA was isolated using BioRad's iScript™ cDNA Synthesis Kit according to the manufacturer's protocol (Catalog No. 1708891). The qPCR reaction was run using SsoAdvanced™ Universal Probes Supermix 1725281 using manufacturer's protocol on the BioRad CFX384 instrument. The TaqMan mouse specific probes were from Invitrogen, MHC I (b2m) Mm00437762_m1 and β-actin Mm01205647_g1 for normalizing gene expression. The delta Ct value for each tumor was calculated for MHC I using β-actin as the reference gene. The expression for MHC I was calculated using the formula 2^-delta Ct for each mouse tumor and this value was divided by its respective final tumor volume at the end of the study.

Figure 6:
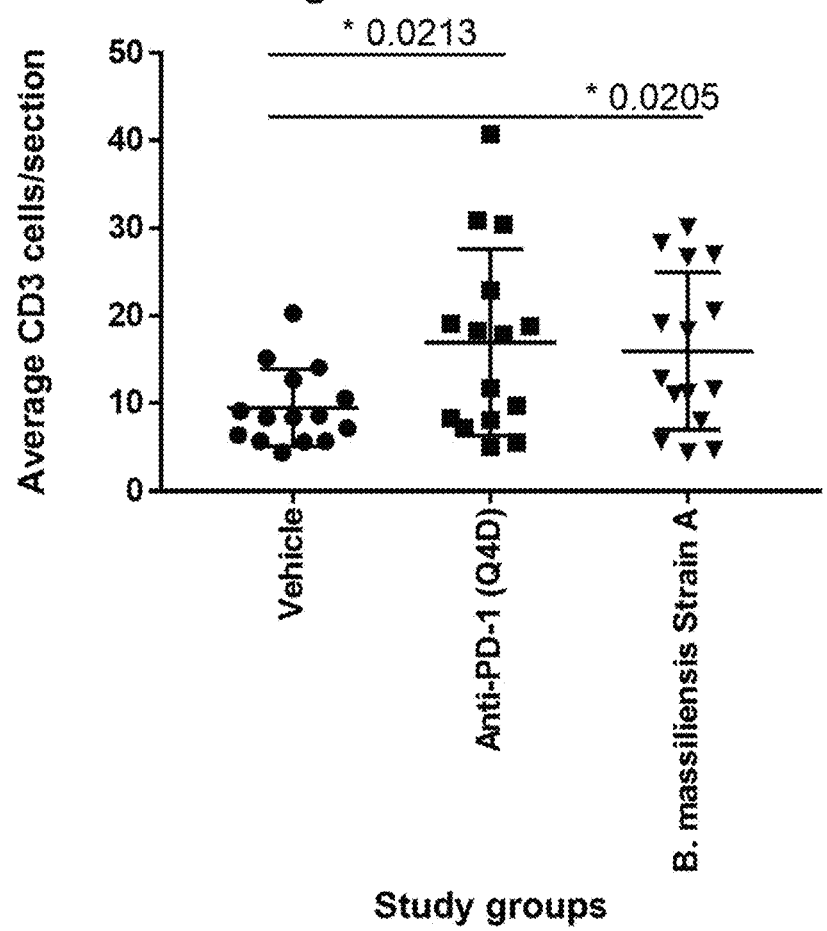
FIG. 6 shows that in a mouse colorectal carcinoma model, the infiltration of CD3+ immune cells was significantly increased in the anti-PD-1 group and the *Blautia massiliensis* Strain A group relative to the vehicle group.
Figure 7:
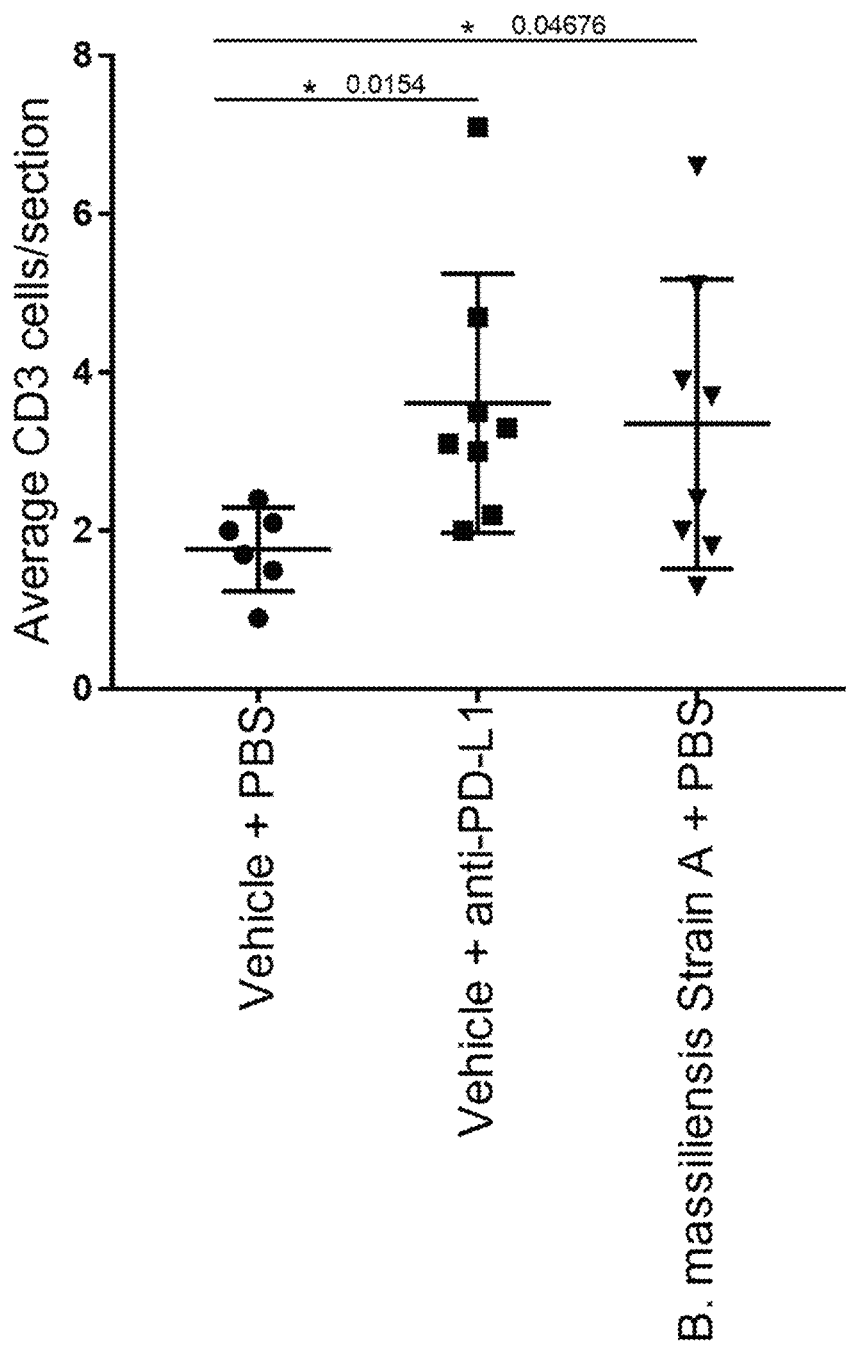
FIG. 7 shows that in a mouse melanoma model, the infiltration of CD3+ immune cells was significantly increased in the anti-PD-L1 group and the *Blautia massiliensis* Strain A group relative to the vehicle group.
Figure 8:
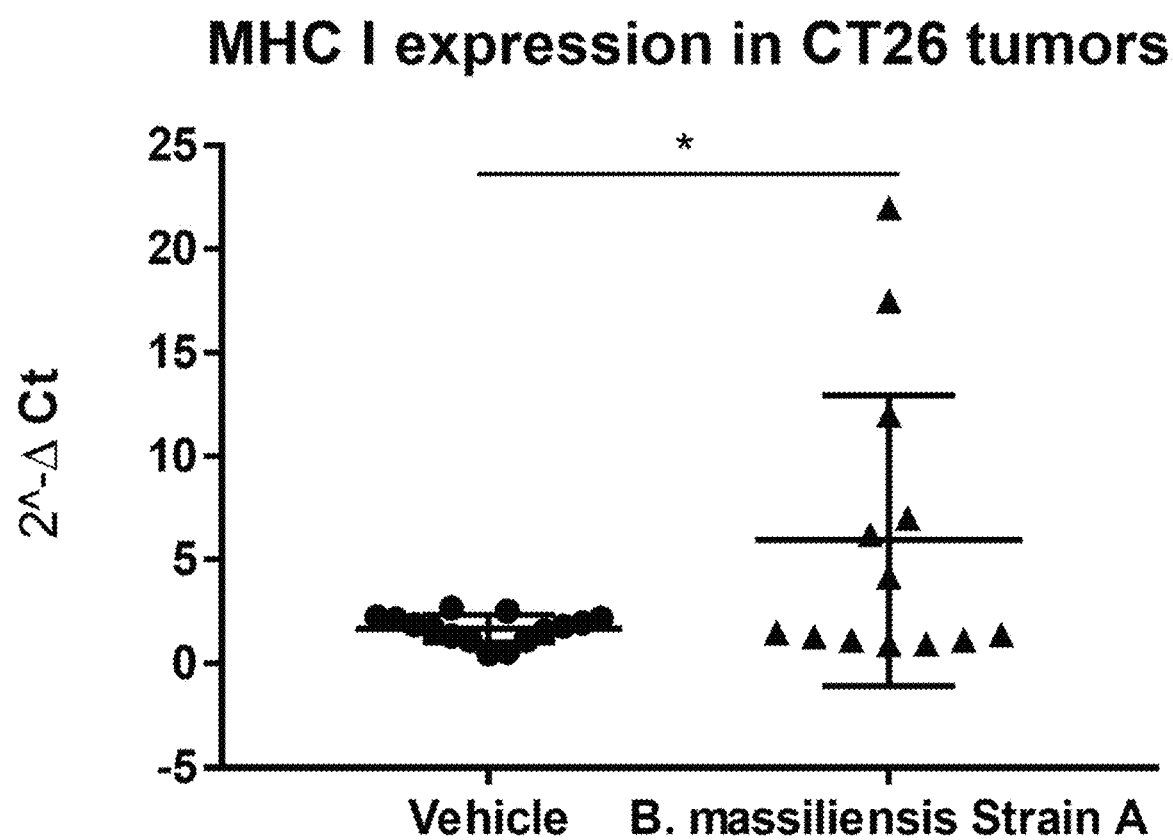
FIG. 8 shows that in a mouse colorectal carcinoma model, *Blautia massiliensis* Strain A induced a striking upregulation of MHC Class I expression relative to the vehicle group.

Tumor volumes were taken prior to CD3+ immune cell infiltrate and MHC Class I expression analysis. Infiltration of CD3+ immune cells was significantly increased in the *Blautia massiliensis* Strain A group relative to vehicle in a mouse colorectal carcinoma model (FIG. 6) and in mouse melanoma model (FIG. 7). *Blautia massiliensis* Strain A induced a striking upregulation of MHC Class I expression (FIG. 8).

Rather than being sacrificed, some mice may be rechallenged with tumor cell injection into the contralateral flank (or other area) to determine the impact of the immune system's memory response on tumor growth.

Example 8: *Blautia* Strain A in a Mouse Lung Cancer Model

*Blautia* Strain A is tested for its efficacy in the mouse lung cancer model, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

$1\times10^6$ LLC1 cells, or an appropriate number of lung cancer cells from another lung cancer cell line, are injected into the hind flank of syngeneic mice. Tumors from the various treatment groups are measured with calipers at regular intervals. Some mice are sacrificed for ex vivo tumor analysis using flow cytometry. Other mice may be rechallenged with tumor cell injection into the contralateral flank to determine the impact of the immune system's memory response on tumor growth.

Example 9: *Blautia* Strain A in a Mouse Breast Cancer Model

*Blautia* Strain A is tested for its efficacy in the mouse breast cancer model, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

4T1 mouse mammary carcinoma cells are obtained from ATCC and $1\times10^6$ cells in 50 ul PBS are injected subcutaneously into one or both hind limbs of Balb/c female mice (as described by Wang et al. 2003, Systemic dissemination of viral vectors during intratumoral injection. Molecular Cancer Therapeutics; 2(11)). Alternatively, EMT6 mouse mammary carcinoma cells are obtained from ATCC and $1\times10^6$ cells in 50 µl PBS are injected subcutaneously into one or both of the hind limbs of Balb/c female mice 6-8 weeks old (as described by Guo et al. 2014, Combinatorial Photothermal and Immuno Cancer Therapy Using Chitosan-Coated Hollow Copper Sulfide Nanoparticles. ASC Nano.; 8(6): 5670-5681). In addition, other available mouse mammary cell lines may be used.

Tumors from the various treatment groups are measured with calipers at regular intervals. *Blautia* Strain A is administered at varied doses at defined intervals. For example, some mice are sacrificed for ex vivo tumor analysis using flow cytometry. Other mice may be rechallenged with tumor cell injection into the contralateral flank to determine the impact of the immune system's memory response on tumor growth.

Alternatively, 4T1 cells can be used in an orthotopic murine model of breast cancer as described by Tao et al. (Tao et al. 2008. Imagable 4T1 model for the study of late stage breast cancer. 8: 288). Mice are sacrificed for ex vivo tumor analysis. Tumors are analyzed by flow cytometry and immunohistochemistry.

Example 10: *Blautia* Strain A in a Mouse Pancreatic Cancer Model

*Blautia* Strain A is tested for its efficacy in the mouse model of pancreatic cancer, either alone or in combination with other cancer therapies, including checkpoint inhibitor(s). Mice are divided into groups receiving *Blautia* Strain A, with or without checkpoint inhibitor treatment. Some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Panc02 cells are maintained in DMEM, supplemented with 10% fetal calf serum and 1% penicillin/streptomycin, and incubated at 37° C. at 5% CO2. Female 8-10 week-old C57Bl/6 mice are obtained from Charles River, Inc. or other certified vendor. Female C57Bl/6 mice are injected subcutaneously into the right hind flank with $1\times10^6$Panc02 cells. This protocol is based on standard Panc02 tumor models (Maletzki et al. 2008. Pancreatic cancer regression by intratumoral injection of live *streptococcus pyogenes* in a syngeneic mouse model. Gut. 57:483-491). Tumors from the various treatment groups are measured with calipers at regular intervals. Some mice are sacrificed for ex vivo tumor analysis using flow cytometry, while other mice are rechallenged to determine the impact of the memory response on tumor growth.

Alternatively, Panc02, 6606PDA, or Capan-1 cells lines can be used in an orthotopic murine model of pancreatic cancer as described by Partecke et al. (Partecke et al. 2011. A syngeneic orthotopic murine model of pancreatic adenocarcinoma in the C57/B16 mouse using the Panc02 and 6606PDA cell lines. Eur. Surg. Res. 47(2):98-107) or Chai et al. (Chai et al. 2013. Bioluminescent orthotopic model of pancreatic cancer progression. J. Vis. Exp. 76: 50395). Mice are sacrificed for ex vivo tumor analysis. Tumors are analyzed by flow cytometry and immunohistochemistry.

Example 11: *Blautia* Strain A in a Mouse Model of Hepatocellular Carcinoma

*Blautia* Strain A is tested for its efficacy in the mouse model of hepatocellular carcinoma, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Hepatocellular carcinoma is induced in mice by subcutaneous inoculation of $1\times10^6$Hepa129 cells (obtained from NCI or other source), or an appropriate number of cells from other hepatocellular carcinoma cell line (as described by Gonzalez-Carmona et al. 2008. CD40 ligand-expressing dendritic cells induce regression of hepatocellular carcinoma by activating innate and acquired immunity in vivo. Hepatology. 48(1):157-168). Tumor cells are inoculated into one or both flanks. Tumors from the various treatment groups are measured with calipers at regular intervals. Some mice are sacrificed for ex vivo tumor analysis using flow

Example 12: *Blautia* Strain A in a Mouse Lymphoma Model

*Blautia* Strain A is tested for its efficacy in the mouse model of lymphoma, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

One lymphoma cell line is the A20 lymphoma, although other lymphoma cell lines may be used with syngeneic mice. A20 lymphoma cells are obtained from ATCC and $5 \times 10^6$ cells in 50 ul PBS are injected subcutaneously into one or both of the hind limbs of Balb/c female mice (as described by Houot et al. 2009. T-cell modulation combined with intratumoral CpG cures lymphoma in a mouse model without the need for chemotherapy. Blood. 113(15): 3546-3552). Tumors from the various treatment groups are measured with calipers at regular intervals. Some mice are sacrificed for ex vivo tumor analysis using flow cytometry, while other mice are rechallenged to determine the impact of the memory response on tumor growth.

Example 13: *Blautia* Strain A in a Mouse Prostate Cancer Model

*Blautia* Strain A is tested for its efficacy in the mouse model of prostate cancer, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Mouse prostate cancer cells ($1 \times 10^5$ RM-1 cells or an appropriate number of cells from another prostate cancer cell line) are injected into syngeneic mice. Tumors from the various treatment groups are measured with calipers at regular intervals. Some mice are sacrificed for ex vivo tumor analysis using flow cytometry, while other mice are rechallenged to determine the impact of the memory response on tumor growth.

Example 14: *Blautia* Strain A in a Mouse Plasmacytoma Model

*Blautia* Strain A is tested for its efficacy in the mouse model of plasmacytoma, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

Mineral Oil Induced Model of Plasmacytoma

To examine the efficacy of *Blautia* Strain A in a plasmacytoma or multiple myeloma model, mice are injected intraperitoneally three times with 500 ul of 2,6,10,12-tetramethylpentadecane ("pristane oil") at various time points between 0 and 60 days, as described by Potter et al. 1983. Peritoneal plasmacytomagenesis in mice: comparison of different pristane dose regimens. J. Natl. Cancer Inst. 71(2): 391-5 (see also Lattanzio et al. 1997. Defective Development of Pristane-Oil Induced Plasmacytomas in Interleukin-6-Deficient BALB/C Mice. Am. J. Pathology: 151(3): 689696). Progression of disease is measured by the degree of abdominal swelling and immune cells and particles in the ascites. Ascites fluid is analyzed for immune cell phenotype by flow cytometry.

Cell-Line Induced Model of Plasmacytoma

To examine the efficacy of *Blautia* Strain A in a plasmacytoma or multiple myeloma model, either MOPC-104E cells or J558 plasmacytoma cells (TIB-6 ATCC) are injected subcutaneously into one or more hind flanks of Balb/c mice ($5 \times 10^6$ cells), based on model described by Bhoopalam et al. 1980. Effect of dextran-S(alpha, 1-3 dextran) on the growth of plasmacytomas MOPC-104E and J558. J. Immunol. 125(4):1454-8 (see also Wang et al. 2015. IL-10 enhances CTL-mediated tumor rejection by inhibiting highly suppressive CD4+ T cells and promoting CTL persistence in a murine model of plasmacytoma. OncoImmunology. 4(7): e1014232-1-9). Mice are divided into groups receiving *Blautia* Strain A by oral gavage, and with or without checkpoint inhibitor treatment. Tumors from the various treatment groups are measured with calipers at regular intervals. Some mice are sacrificed for ex vivo tumor analysis using flow cytometry, while other mice are rechallenged to determine the impact of the memory response on tumor growth.

Example 15: *Blautia* Strain A in a SCID Mouse Model of Mouse Myeloma

*Blautia* Strain A is tested for its efficacy in the SCID mouse model of myeloma, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm$^3$) and treatment is then initiated accordingly.

To examine the efficacy of *Blautia* Strain A using a human plasma cell leukemia, 1×10⁷ human myeloma cell lines, ARH77 cells (ARH77-ATCC CRL-1621, or an appropriate number of cells from another myeloma cell line such as KPMM2) are used. Myeloma cells are injected subcutaneously into one or both hind flanks of SCID mice (See Caers et al. 2004. Of mice and men: disease models of multiple myeloma. Drug Discovery Today: Disease Models. 1(4): 373-380. Tumors from the various treatment groups are measured with calipers at regular intervals. Some mice are sacrificed for ex vivo tumor analysis using flow cytometry, while other mice are rechallenged to determine the impact of the memory response on tumor growth.

Example 16: *Blautia* Strain A in a Mouse Renal Cell Carcinoma Model

*Blautia* Strain A is tested for its efficacy in the mouse model of renal cell carcinoma, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm³) and treatment is then initiated accordingly.

To examine the efficacy of *Blautia* Strain A in a mouse model of renal cell carcinoma, Renca cells (ATCC CRL-2947) or other renal cell carcinoma cells are injected subcutaneously into one or both flanks of 7-8 week old syngeneic Balb/c mice (5×10⁶ in 0.1 ml PBS). Tumors from the various treatment groups are measured with calipers at regular intervals. Some mice are sacrificed for ex vivo tumor analysis using flow cytometry, while other mice are rechallenged to determine the impact of the memory response on tumor growth.

Example 17: *Blautia* Strain A in a Mouse Bladder Cancer Model

*Blautia* Strain A is tested for its efficacy in the mouse model of bladder cancer, either alone or in combination with other cancer therapies, including checkpoint inhibitor(s). Mice are divided into groups receiving *Blautia* Strain A, with or without checkpoint inhibitor treatment. *Blautia* Strain A is administered at varied doses at defined intervals. For example, some mice receive *Blautia* Strain A (p.o.) on the day following tumor cell injection (day 1). Some mice receive seven (7) consecutive doses of *Blautia* Strain A (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm³) and treatment is then initiated accordingly.

On the day of inoculation, MBT-2 cells (or other bladder cancer cell line) are harvested and resuspended in 1:1 PBS/Matrigel mixture. 2×10⁵ MBT-2 cells are suspended in 100 ul of mixture and injected subcutaneously into one or both hind flanks of syngeneic mice. Tumors are measured with calipers at regular intervals.

Some mice are sacrificed for ex vivo tumor analysis using flow cytometry, while other mice are rechallenged to determine the impact of the memory response on tumor growth.

Example 18: The Efficacy of a *Blautia* Strain A Strain is Compared to Other *Blautia* Strains for Efficacy in Cancer Models Using methods described above, various *Blautia* Strain A and other *Blautia* strains are tested and compared for efficacy in various cancer models. Such models may include, but are not limited to, melanoma, lung cancer, breast cancer, colon cancer, colorectal cancer, pancreatic cancer, hepatocellular cancer, lymphoma, prostate cancer, plasmacytoma, a SCID model of myeloma, renal cell carcinoma, and/or bladder cancer.

Example 19: An Open-Label Study of the Safety, Tolerability and Efficacy of a *Blautia* Strain A Oral Therapeutic in Patients with Metastatic Colorectal Carcinoma A multi-center, open-label clinical study with dose escalations and dose expansions to assess preliminary safety, tolerability, and efficacy of the *Blautia* Strain A is performed. The study proceeds in three parts: Part A: Dose escalation in microsatellite stable (MSS) metastatic colorectal carcinoma (CRC) and alternative indications, Part B: MSS CRC and alternative indications, and Part C: microsatellite instable (MSI) CRC. Dose escalation occurs in a standard 3+3 design, as set forth in Table 4. In part A, from 9 to 18 patients are enrolled. Parts B and C are enrolled concurrently. In Part B, up to 15 and no fewer than 10 patients are enrolled. In Part C no fewer than 5 and up to 10 patients are enrolled. Based on in vivo studies of allograft bearing mice, an exemplary estimated human effective dose is 2×10¹¹ organisms per day, delivered per enteric capsule.

The primary objectives of the study include the determination of the maximum tolerated dose within the tested dose range for *Blautia* Strain A in patients with advanced malignancies; the determination of the recommended phase 2 dose for *Blautia* Strain A in CRC; the evaluation of the safety and tolerability, including dose limiting toxicities of *Blautia* Strain A; and the demonstration of anti-tumor activity of *Blautia* Strain A in patients with CRC (MSI and MSS). The anti-tumor activity will be assessed by monitoring changes in circulating tumor cells, immune cell subsets in blood and tumor, and tumor viability; objective response rate and duration of response; progression-free survival; overall survival; clinical benefit rate and duration of clinical benefit rate; and disease control rate and duration of disease control rate. The secondary objective is to determine the human distribution and elimination of *Blautia* Strain A. The exploratory objectives is to evaluate correlations of *Blautia* Strain A response with molecular markers relevant to each tumor type and to identify possible mechanisms of resistance to *Blautia* Strain A.

Inclusion and Exclusion Criteria:

The inclusion criteria for all parts of the study include the following:
1. Written informed consent obtained prior to any screening procedures and in accordance with federal, local, and institutional guidelines.
2. Age ≥18 years.
3. Adequate hepatic function:
    a. total bilirubin ≤2 times the upper limit of normal (ULN) (except patients with Gilbert's syndrome

[hereditary indirect hyperbilirubinemia] who must have a total bilirubin of ≤3 times ULN),
   b. aspartate aminotransferase (AST) and alanine aminotransferase (ALT)≤2.5 times ULN (except patients with known liver involvement of their tumor who must have their AST and ALT ≤5.0 times ULN).
4. Adequate renal function: estimated creatinine clearance of ≥30 mL/min, calculated using the formula of Cockcroft and Gault (140−Age)·Mass (kg)/(72·creatinine mg/dL); multiply by 0.85 if female.
5. All patients in part B+C must be willing to have fresh biopsies at start of therapy and after 4 weeks of therapy.
6. Contraception: Female patients of child-bearing potential must agree to use dual methods of contraception (including one highly effective and one effective method of contraception) and have a negative serum pregnancy test at Screening, and male patients must use an effective barrier method of contraception if sexually active with a female of child-bearing potential. For both male and female patients, effective methods of contraception must be used throughout the study and for 3 months following the last dose.

For the portions of the study testing relapsed/refactory colorectal cancer, the inclusion criteria also include the following:

7. Histological or cytological documentation of adenocarcinoma of the colon or rectum.
8. Known MSI/MSS status.
9. Measurable disease by RECIST v1.1.
10. Metastatic disease not suitable for upfront curative-intent surgery.
11. Documented evidence of progressive disease according to RECIST v1.1.
12. Prior treatment (with completion of a course of therapy, or to disease progression or intolerability) with each of the following:
   a. Fluoropyrimidine-, oxaliplatin-, irinotecan-based chemotherapies (e.g., FOLFOX and FOLFIRI)
   b. if KRAS wild-type, an anti-EGFR therapy,
   c. Regorafenib or TAS 102 (Past A required, parts B+C optional)
   d. Radiation and surgery are not considered as prior anticancer regimens
13. Patients should not be transfusion dependent.
14. Adequate hematopoietic function: ANC≥1000/mm3, hemoglobin (Hb)≥9.0 g/dL, and platelet count ≥100,000/mm3.
15. Eastern Cooperative Oncology Group (ECOG) performance status of ≤1.
16. Life expectancy of ≥3 months.

The following categories of patient are excluded from the study:

1. Female patients who are pregnant or lactating.
2. Major surgery within 4 weeks before C1D1.
3. Impaired cardiac function or clinically significant cardiac diseases, including any of the following:
   a. Unstable angina or acute myocardial infarction ≤3 months prior to C1D1;
   b. Clinically significant heart disease (e.g., symptomatic congestive heart failure [e.g., >NYHA Class 2]; uncontrolled arrhythmia, or hypertension; history of labile hypertension or poor compliance with an antihypertensive regimen).
4. Uncontrolled active severe systemic infection requiring parenteral antibiotics, antivirals, or antifungals within one week prior to C1D1.
5. Any ongoing antibiotic treatment which has not been discontinued at least 3 days prior to initiation of therapy
6. Patients with known symptomatic brain metastasis are not suitable for enrollment. Patients with asymptomatic, stable, treated brain metastases are eligible for study entry.
7. Patients with a known history of human immunodeficiency virus (HIV); HIV testing is not required as part of this study.
8. Known, active hepatitis A, B, or C infection; or known to be positive for HCV RNA or HBsAg (HBV surface antigen).
9. Prior malignancies:
   a. Patients with adequately resected basal or squamous cell carcinoma of the skin, or adequately resected carcinoma in situ (i.e. cervix) may enroll irrespective of the time of diagnosis.
   b. Prior malignancies which may interfere with the interpretation of the study. Cancer treated with curative intent <5 years previously will not be allowed unless approved by the Sponsor. Cancer treated with curative intent >5 years previously and without evidence of recurrence will be allowed.
10. Patients with active central nervous system (CNS) malignancy. Patients who have only had prophylactic intrathecal or intravenous chemotherapy against CNS disease are eligible.
11. Patients with gastrointestinal tract disease (or uncontrolled vomiting or diarrhea) that could interfere with the absorption of EVP001.
12. Serious psychiatric or medical conditions that, in the opinion of the Investigator, could interfere with treatment, compliance, or the ability to give consent.
13. Patients unwilling to comply with the protocol including required biopsies and sample collections required to measure disease.
14. Radiotherapy within two weeks prior to screening. Patients must have recovered from clinically significant toxicities.

The use of any concomitant medication/therapy, including over-the-counter (OTC) medications deemed necessary for the care of the patient is permitted during the study. Medications required to treat AEs, manage cancer symptoms, concurrent stable diseases and supportive care agents (e.g. blood product transfusions), pain medications, anti-emetics, and anti-diarrheals are allowed. Concurrent therapy with growth factors is allowed. The use of any immunosuppressive agents must be discussed between the Investigator and the Medical Monitor on a case-by-case basis. Any diagnostic, therapeutic, or surgical procedure performed during the study period should be recorded, including the dates, description of the procedure(s), and any clinical findings, if applicable. All antibiotics are contraindicated.

Hormonal contraceptives are permitted in women of child-bearing potential. Hormonal contraceptives include any marketed contraceptive agent that includes an estrogen and/or a progestational agent.

Investigational or commercial anticancer agents other than *Blautia* Strain A is not allowed during the study. The initiation of any non-protocol specific anti-tumor treatment is considered an indication of disease relapse/progression and should be recorded appropriately in the electronic case report forms.

Palliative radiation therapy to non-target lesions is permitted but study treatment is held for ≥1 day before the start of palliative radiation therapy and ≥1 day following each dose of palliative radiation therapy. Treatment with *Blautia* Strain A is not discontinued solely due to palliative radiation.

Supportive measures for optimal medical care should be provided to patients during participation in this study. These should be based on institutional and/or National Comprehensive Cancer Network (NCCN) guidelines.

Dose Escalation Study

Patients receive all *Blautia* Strain A doses during the 7 day treatment period, or have had a dose-limiting toxicity (DLT) within the treatment period to be considered evaluable for dose escalation decisions. *Blautia* Strain A is orally administered as tablets or enteric coated capsules. Dose escalation decisions occur when the cohort of patients has met these criteria.

A DLT is defined as an adverse event (AE) or abnormal laboratory value that occurs within the first 7 days of treatment with *Blautia* Strain A, except for those that are clearly and incontrovertibly due to underlying disease, disease progression, or extraneous causes, and meets any of the criteria included in Table 7. National Cancer Institute Common Terminology Criteria for Adverse Events (NCI CTCAE) (Version 4.03) is used for all grading. In addition, >4 missed doses of *Blautia* Strain A will be considered a DLT. Dose escalation decisions occur when the cohort of patients has met these criteria.

TABLE 7

Criteria for defining DLT

| Toxicity | Any of the following criteria (based on CTCAE [Version 4.03]): |
|---|---|
| Non-Hematologic | Grade ≥ 3 nausea/vomiting, while taking optimal supportive medications. |
| | Any other Grade ≥ 3 non-hematological toxicity except alopecia or electrolyte abnormalities correctable with supportive therapy. |
| Hematologic | Grade 4 neutropenia lasting more than 5 days. |
| | Febrile neutropenia (absolute neutrophil count [ANC] < 1 × 10$^9$/L, fever > 38.5° C.). |
| | Grade 4 thrombocytopenia, or Grade 3 thrombocytopenia with bleeding, or any requirement for platelet transfusion. |

CTCAE Version 4.03 will be used for grading all AEs and laboratory abnormalities.
Patients may receive supportive care as per local institutional guidelines.

To implement dose escalation decisions, the available toxicity information (i.e., all AEs and all laboratory abnormalities regardless of DLT assessment) is evaluated by the enrolling Investigators and Sponsor medical monitor at a dose decision meeting or teleconference. Decisions are based on an evaluation of all relevant data available from all dose cohorts evaluated in the ongoing study including safety information, DLTs, all NCI CTCAE, Version 4.03 toxicity data during Cycle 1 from evaluable patients. Drug administration at the next higher dose cohort may not proceed until the Investigator receives written confirmation from Sponsor indicating that the results of the previous dose cohort were evaluated and that it is permissible to proceed to the next higher dose cohort.

Table 8 below describes the starting dose and the dose levels that may be evaluated during the study for all parts of the study.

TABLE 8

*Blautia* Strain A Dose Escalation Levels

| Cohort | Dose Levels QD dosing; 3 week cycles | Number of Patients |
|---|---|---|
| 1 | 2 × 10$^8$ organisms | 3 + 3 |
| 2 | 1 × 10$^9$ organisms | 3 + 3 |
| 3 | 2 × 10$^9$ organisms | 3 + 3 |
| 4 (optional) | 4 × 10$^9$ organisms | 3 |

A standard 3+3 dose escalation is conducted as follows:

If 0 of 3 patients experiences a DLT, escalate to next higher dose cohort.

If 1 of 3 patients experiences a DLT, that cohort will be expanded to 6 patients. If 1 of 6 patients experiences a DLT, escalate to the next higher dose cohort;

If ≥2 of 3 or ≥2 of 6 patients experience a DLT, the maximum tolerated dose (MTD) is exceeded.

If the MTD is exceeded, enrollment of additional patients will be at a lower dose level. If a starting dose does not clear DLT assessment, dose de-escalation will proceed using standard 3+3 rules Intra-patient dose escalations are permitted for all cohorts after the intended dose level has been shown to be safe (i.e., all patients treated at the intended dose level completed DLT assessments and ≤1 patient experienced a DLT).

For dose escalation patients after 7 days and dose expansion patients, if an event meeting the definition of a DLT, but without necessarily occurring within the first 21 days, is observed in >33% of patients at any time, or if >33% of treated patients have withdrawn consent due to toxicity, enrollment will be held and a meeting with all Investigators and Sponsor will take place to review the events and discuss their clinical significance. Based on this review, the Sponsor may elect to reduce the dose for enrolled patients and to resume enrollment of the expansion cohort at this lower dose, or the enrollment into the expansion cohort may be stopped.

Safety and tolerability are evaluated by means of DLTs (dose escalation cohorts only), AE reports, physical examinations, electrocardiograms and laboratory safety evaluations.

Anti-tumor activity are assessed by the Investigator according to disease specific response criteria and described in terms of objective response rate, duration of response, progression-free survival, clinical benefit rate, overall survival, and disease control rate.

In Part A: Peripheral blood WBC subsets and cytokines are analyzed at baseline and 7 days. Cytokines are additionally analyzed at 24 and 48 hours.

In Parts B and C: Peripheral blood WBC subsets and cytokines are analyzed at baseline and 7 and 21 days. Baseline and day 28 tumor biopsies are analyzed for immune subset infiltration, as well as makers of angiogenesis, proliferation, and death.

Patients continue to receive *Blautia* Strain A until the patient has confirmed pharmacodynamics, withdraws consent, is lost to follow-up, experiences intolerable toxicity which precludes further treatment with *Blautia* Strain A, or treatment is discontinued at the discretion of the patient, Investigator, or Sponsor. Patients who have objective disease progression but have evidence of overall clinical benefit may, at the request of the treating physician, continue treatment with *Blautia* Strain A after discussion with the Medical Monitor.

INCORPORATION BY REFERENCE

All publications patent applications mentioned herein are hereby incorporated by reference in their entirety as if each individual publication or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inducing an anti-tumor immune response in a subject comprising orally administering to the subject an effective amount of a bacterial composition comprising *Blautia* Strain A (ATCC Deposit Number PTA-125134) wherein the subject has a tumor.

2. The method of claim 1, wherein the tumor is a renal cell carcinoma, bladder cancer, prostate cancer, lung cancer, colon cancer, colorectal cancer, melanoma, breast cancer, pancreatic cancer or hepatocellular carcinoma tumor.

3. The method of claim 1, wherein at least 50% of the bacteria in the bacterial composition are *Blautia* Strain A.

4. The method of claim 1, wherein substantially all at least 99% of the bacteria in the bacterial composition are *Blautia* Strain A.

5. The method of claim 1, wherein the bacterial composition comprises at least $1\times10^6$ colony forming units (CFUs) of *Blautia* Strain A.

6. The method of claim 1, wherein the bacterial composition further comprises a pharmaceutically acceptable carrier.

7. The method of claim 1, wherein the bacterial composition is formulated as a capsule or a tablet.

8. The method of claim 7, wherein the capsule or tablet comprises an enteric coating.

9. The method of claim 8, wherein at least 99% of the bacteria in the bacterial composition are *Blautia* Strain A.

10. The method of claim 9, wherein the bacterial composition comprises at least $2\times10^8$ organisms of *Blautia* Strain A.

11. The method of claim 1, wherein the bacterial composition comprises live bacteria, attenuated bacteria, or killed bacteria.

12. The method of claim 1, wherein the method further comprises administering to the subject a second cancer therapy.

13. The method of claim 12, wherein the second cancer therapy comprises the administration of a chemotherapy agent to the subject.

14. The method of claim 12, wherein the second cancer therapy comprises administering an antibiotic to the subject.

15. The method of claim 1, wherein the method further comprises administering a prebiotic to the subject.

* * * * *